US011019005B2

(12) United States Patent
Bulut et al.

(10) Patent No.: US 11,019,005 B2
(45) Date of Patent: May 25, 2021

(54) PROXIMITY TRIGGERED SAMPLING

(71) Applicant: KONINKLIJKE PHILIPS N.V., Eindhoven (NL)

(72) Inventors: Murtaza Bulut, Eindhoven (NL); Aart Tijmen Van Halteren, Geldrop (NL)

(73) Assignee: Koninklijke Philips N.V., Eindhoven (NL)

(*) Notice: Subject to any disclaimer, the term of this patent is extended or adjusted under 35 U.S.C. 154(b) by 87 days.

(21) Appl. No.: 16/022,748

(22) Filed: Jun. 29, 2018

(65) Prior Publication Data

US 2019/0007354 A1     Jan. 3, 2019

Related U.S. Application Data

(60) Provisional application No. 62/527,087, filed on Jun. 30, 2017.

(51) Int. Cl.
| | |
|---|---|
| *H04L 12/58* | (2006.01) |
| *H04L 29/08* | (2006.01) |
| *G16H 10/20* | (2018.01) |
| *G16H 40/63* | (2018.01) |
| *G16H 50/20* | (2018.01) |

(52) U.S. Cl.
CPC ........... *H04L 51/046* (2013.01); *G16H 10/20* (2018.01); *G16H 40/63* (2018.01); *G16H 50/20* (2018.01); *H04L 51/34* (2013.01); *H04L 67/18* (2013.01); *H04L 51/20* (2013.01)

(58) Field of Classification Search
CPC ....... H04L 51/046; H04L 51/34; H04L 67/18; H04L 51/20; G16H 50/20; G16H 40/63; G16H 10/20
See application file for complete search history.

(56) References Cited

U.S. PATENT DOCUMENTS

| | | | | |
|---|---|---|---|---|
| 8,739,282 | B1* | 5/2014 | Jayaraman | G06F 11/0709 726/22 |
| 9,386,401 | B2 | 7/2016 | Gold | |
| 2004/0153214 | A1* | 8/2004 | Ader | A61M 5/16827 700/282 |
| 2008/0161715 | A1* | 7/2008 | Stivoric | A61B 5/0008 600/549 |
| 2011/0245633 | A1* | 10/2011 | Goldberg | A61B 5/681 600/301 |
| 2014/0377727 | A1* | 12/2014 | Yom-Tov | G06F 16/951 434/236 |
| 2015/0140527 | A1 | 5/2015 | Gilad-Barach | |
| 2015/0313529 | A1* | 11/2015 | Nevo | A61B 5/22 600/595 |
| 2016/0057565 | A1* | 2/2016 | Gold | H04W 4/80 455/41.1 |
| 2016/0321403 | A1* | 11/2016 | Wang | G16H 10/60 |

(Continued)

FOREIGN PATENT DOCUMENTS

WO    WO2010138975 A1    12/2010

*Primary Examiner* — Backhean Tiv
*Assistant Examiner* — Jihad K Boustany

(57) ABSTRACT

In one embodiment, a computer-implemented method comprising receiving data corresponding to an interaction with a user; based on the received data, predicting a moment in time when a state of the user is likely to change; and causing a change in one or a combination of message function characteristics or data collection function characteristics at the moment in time.

24 Claims, 8 Drawing Sheets

(56) References Cited

U.S. PATENT DOCUMENTS

| | | | |
|---|---|---|---|
| 2016/0373490 A1* | 12/2016 | Sedar | H04L 65/1069 |
| 2017/0049374 A1* | 2/2017 | Eldardiry | A61B 5/165 |
| 2018/0132776 A1* | 5/2018 | Flickinger | A61B 5/6898 |
| 2018/0220973 A1* | 8/2018 | Asianto | A61B 5/11 |
| 2018/0311573 A1* | 11/2018 | Pickover | A63F 13/25 |

* cited by examiner

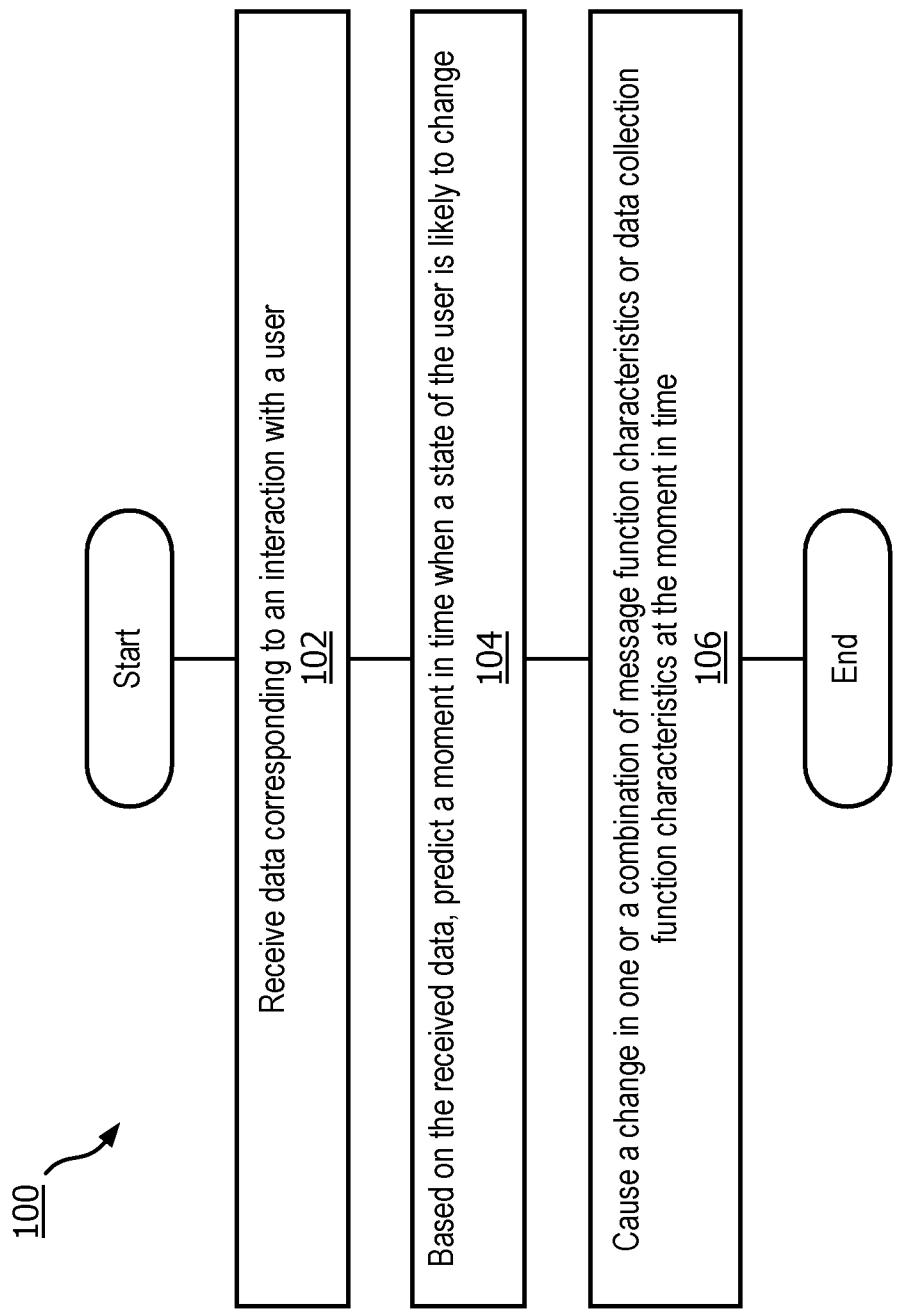

PROXIMITY TRIGGERED SAMPLING

CROSS-REFERENCE TO RELATED APPLICATIONS

This patent application claims the priority benefit under 35 U.S.C. § 119(e) of U.S. Provisional Application No. 62/527,087 filed on Jun. 30, 2017, the contents of which are herein incorporated by reference.

FIELD OF THE INVENTION

The present invention is generally related to digital devices and systems, and in particular, messaging using digital devices.

BACKGROUND OF THE INVENTION

Healthcare is beginning a dramatic transformation as the technologies of the Information Age are starting to be implemented to improve outcomes and lower costs. As part of that transformation, healthcare is becoming more industrialized. More data than ever before is being collected about the health and wellness of people, and this data is being used to drive better diagnoses and results based on what works across large populations. Best practices are being shared across hospitals and geographic regions. At the same time, healthcare is becoming more personalized. For example, therapies are being tailored based on an individual's genetics to make sure the best treatment for that individual is used. Finally, patients and caregivers are approaching their healthcare as consumers. In the healthcare system, they want the ease, convenience, and simplicity that they already experience in the online retail and financial space.

Despite those drivers of change in the healthcare space, it can be very challenging to gather the data that actually furthers those aims, especially in the case of getting data related to a person's lifestyle. An experience sampling method (ESM), also referred to as a daily diary method, or ecological momentary assessment (EMA), is a research methodology that asks participants to stop at certain times and make notes of their experience in real time. It is desirable to find the right moments to conduct ecological momentary assessments (EMA) or interventions (EMI) (or in general to make certain functionalities available) to the users of a mobile device. Interventions may be in the form of electronic messages, and such timely messages may be a one-way communication message (e.g. information cards), without requiring the user to provide any direct input, two-way communication messages (e.g., mood rating questionnaires) where a user response is expected, or requiring user input to activate certain functionality (e.g., start or stop heart rate (HR) measurements) in a device. A current method for finding the right intervention moments is based on sampling at pre-determined or random moments and monitoring the user behavior and response rate with the help of the data mining tools. Such methods provide moments that are optimal across a population, but are likely to be sub-optimal on an individual level. Some examples include the use of a card-based system for interacting with users of the Philips Healthwatch, where messages are presented as cards. In most cases these cards are one-way messages (e.g., informational), but in some cases a card poses a question to the user. The timing of the message may vary depending on the difference between one that is utilized by the user in an impactful way and one that is ignored.

SUMMARY OF THE INVENTION

In one embodiment, a computer-implemented method comprising receiving data corresponding to an interaction with a user; based on the received data, predicting a moment in time when a state of the user is likely to change; and causing a change in one or a combination of message function characteristics or data collection function characteristics at the moment in time.

These and other aspects of the invention will be apparent from and elucidated with reference to the embodiment(s) described hereinafter.

BRIEF DESCRIPTION OF THE DRAWINGS

Many aspects of the invention can be better understood with reference to the following drawings, which are diagrammatic. The components in the drawings are not necessarily to scale, emphasis instead being placed upon clearly illustrating the principles of the present invention. Moreover, in the drawings, like reference numerals designate corresponding parts throughout the several views.

FIG. 8 is a flow diagram that illustrates an example proximity triggered sampling method, in accordance with an embodiment of the invention.

DETAILED DESCRIPTION OF EMBODIMENTS

Figure 1:
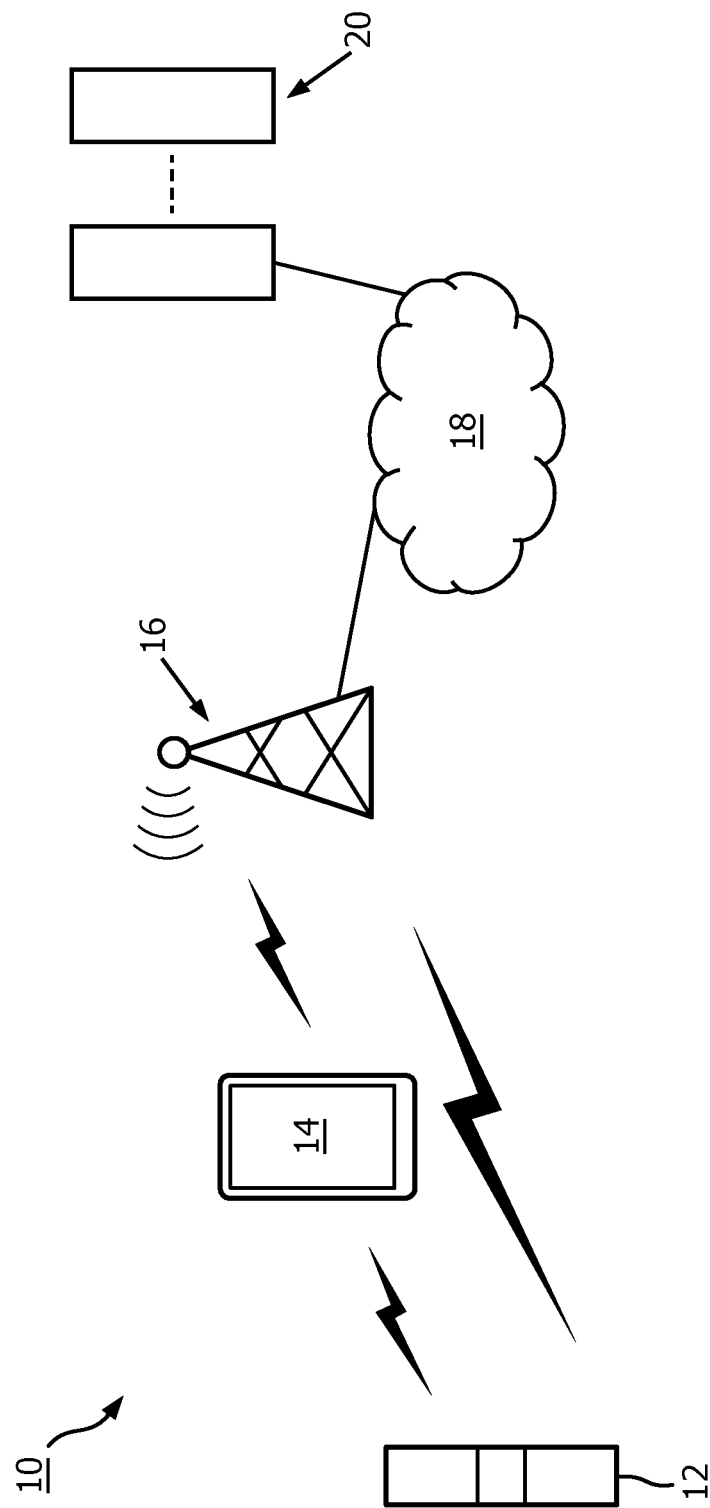
FIG. 1 is a schematic diagram that illustrates an example environment in which a proximity triggered sampling system is used, in accordance with an embodiment of the invention.

Disclosed herein are certain embodiments of a proximity triggered sampling system, apparatus, and method (also collectively referred to herein as a proximity triggered sampling system) that determine the best moments to intervene in a user's life with messaging via a user device. In one embodiment, the proximity triggered sampling system determines the best moments by finding meaningful sampling moments via user state monitoring using data (e.g., proximity data). In other words, the proximity triggered sampling system samples the psychological (and/or physiological) state of a person in relation to social interactions, from there determining the best moments to intervene with questions, content, and/or to change device functionality characteristics. For instance, the proximity triggered sampling system may monitor if the person is alone, or together with someone, to determine the moments to send mood questionnaires.

Digressing briefly, existing systems start sampling at random (or calculated) times to find the right moments to intervene, and once a sufficient amount of data has been collected, to use this data to predict/calculate new times, which is not an optimal method. For instance, random sampling requires many observations, which means a large amount of user sampling to find the best intervention moments. Since the sampling moments are selected randomly, it is highly likely that the user state has not changed, which limits the information that can be learned from the sampling. Certain embodiments of a proximity triggered sampling system, in contrast, predict the moments where user state (e.g. psychological and/or physiological) is likely to change, and increase the sampling frequency at these meaningful moments, or sample only at these moments. For example, for an ecological momentary assessment (EMA) that includes a mood monitoring questionnaire, predicting the moments of potential user emotional state change, and using these moments to trigger user sampling (e.g., an EMA) is a better and more effective method. One challenge to this approach is (to learn) to automatically predict the meaningful moments, where the user's emotional state is likely to change. With certain embodiments of a proximity triggered sampling system, one solution, supported by preliminary experimental data, is based on observing the user with, in some instances, the same device that delivers the EMAs (hence not always requiring additional sensors) to find better moments for sampling the user.

Having summarized certain features of a proximity triggered sampling system of the present disclosure, reference will now be made in detail to the description of a proximity triggered sampling system as illustrated in the drawings. While a proximity triggered sampling system will be described in connection with these drawings, there is no intent to limit the proximity triggered sampling system to the embodiment or embodiments disclosed herein. For instance, though described primarily in the context of directly soliciting user input using questions (e.g., two-way communication messages), certain embodiments of a proximity triggered sampling system may be used to push information to the user at the meaningful moments (e.g., a one-way communication message, including information cards, that do not require the user to provide input) and/or change (e.g., activate, increase, decrease) data collection functionality characteristics (e.g., start or stop a heart rate measurement, sampling frequency, memory capacity, etc.) of the main communication device or other accompanying devices or software linked to the main communication device. Further, although the description identifies or describes specifics of one or more embodiments, such specifics are not necessarily part of every embodiment, nor are all various stated advantages necessarily associated with a single embodiment or all embodiments. On the contrary, the intent is to cover all alternatives, modifications and equivalents consistent with the disclosure as defined by the appended claims. Further, it should be appreciated in the context of the present disclosure that the claims are not necessarily limited to the particular embodiments set out in the description.

Figure 2:
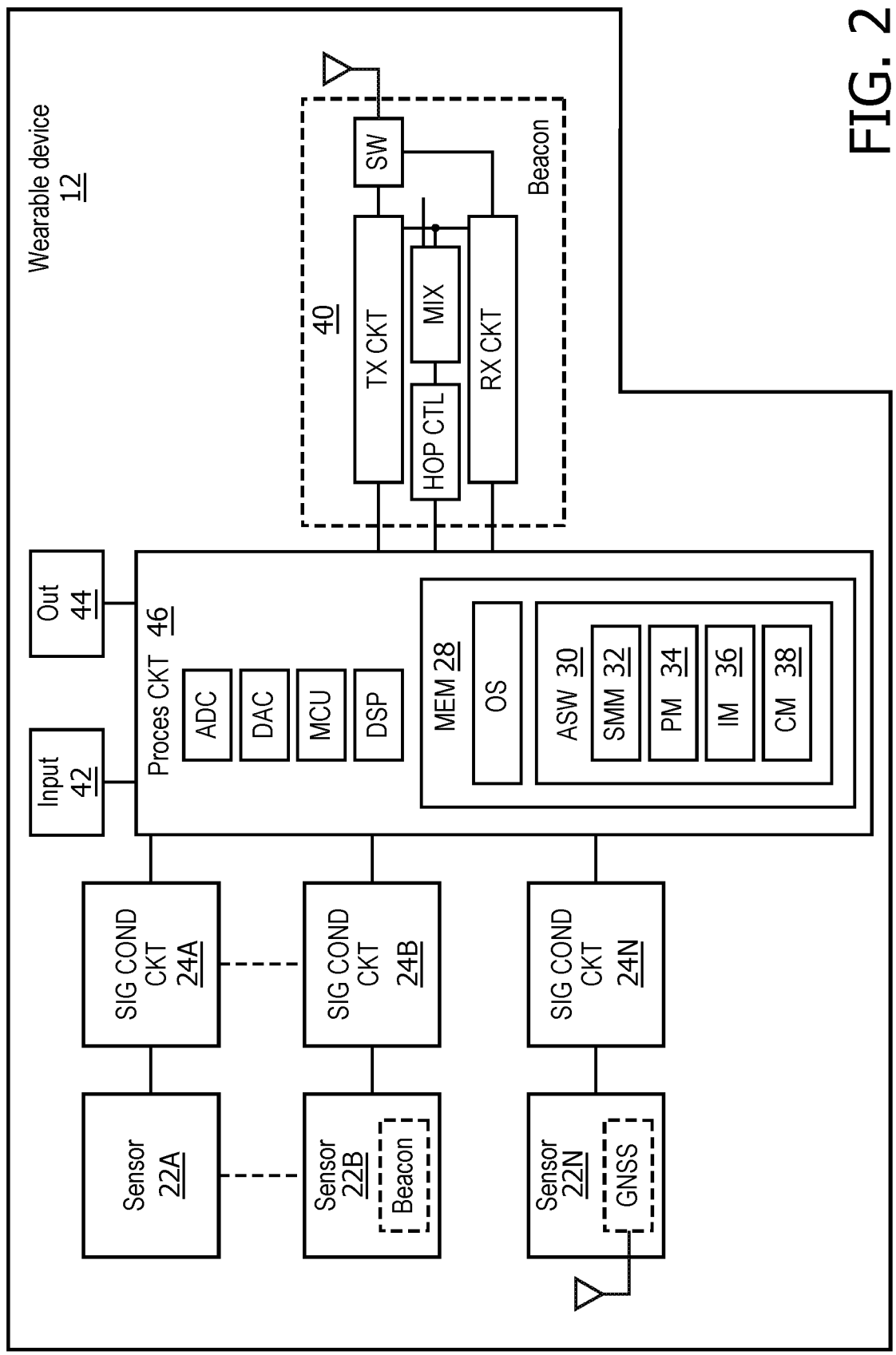
FIG. 2 is a schematic diagram that illustrates an example wearable device in which all or a portion of the functionality of a proximity triggered sampling system may be implemented, in accordance with an embodiment of the invention.

Referring now to FIG. 1, shown is an example environment 10 in which certain embodiments of a proximity triggered sampling system may be implemented. It should be appreciated by one having ordinary skill in the art in the context of the present disclosure that the environment 10 is one example among many, and that some embodiments of a proximity triggered sampling system may be used in environments with fewer, greater, and/or different components that those depicted in FIG. 1. The environment 10 comprises a plurality of devices that enable communication of information throughout one or more networks. The depicted environment 10 comprises a wearable device 12, an electronics device 14, a cellular network 16, a wide area network 18 (e.g., also described herein as the Internet), and a remote computing system 20 comprising one or more computing devices and/or storage devices. Note that the wearable device 12 and the electronics device 14 are also referred to as user devices. The wearable device 12, as described further in association with FIG. 2, is typically worn by the user (e.g., around the wrist or torso or attached to an article of clothing), and comprises a plurality of sensors that track physical activity of the user (e.g., steps, swim strokes, pedaling strokes, sports activities, etc.), sense/measure or derive physiological parameters (e.g., heart rate, respiration, skin temperature, etc.) based on the sensor data, and optionally sense various other parameters (e.g., outdoor temperature, humidity, location, etc.) pertaining to the surrounding environment of the wearable device 12. For instance, in some embodiments, the wearable device 12 may comprise a global navigation satellite system (GNSS) receiver (and associated positioning software and antenna(s)), including a GPS receiver, which tracks and provides location coordinates (e.g., latitude, longitude, altitude) for the device 12. Other information associated with the recording of coordinates may include speed, accuracy, and a time stamp for each recorded location. In some embodiments, the location information may be in descriptive form, and geofencing (e.g., performed locally or external to the wearable device 12) is used to transform the descriptive information into coordinate numbers. In some embodiments, the wearable device 12 may comprise indoor location or proximity sensing technology, including beacons, RFID or other coded light technologies, Wi-Fi, etc. In some embodiments, GNSS functionality may be performed at the electronics device 14 in addition to, or in lieu of, such functionality being performed at the wearable device 12. Some embodiments of the wearable device 12 may include a motion or inertial tracking sensor, including an accelerometer and/or a gyroscope, providing movement data of the user (e.g., to detect limb movement and type of limb movement to facilitate the determination of whether the user is engaged in sports activities, stair walking, or bicycling, or the provision of other contextual data). A representation of such gathered data may be communicated to the user via an integrated display on the wearable device 12 and/or on another device or devices. In some embodiments, the wearable device 12 may be embodied as a virtual reality device or an augmented reality device. In some embodiments, the wearable device 12 may be embodied as an implantable, which may include biocompatible sensors that reside underneath the skin or are implanted elsewhere.

Also, such data gathered by the wearable device 12 may be communicated (e.g., continually, periodically, and/or aperiodically, including upon request) to one or more electronics devices, such as the electronics device 14 or to the computing system 20 via the cellular network 16. Such communication may be achieved wirelessly (e.g., using near field communications (NFC) functionality, Blue-tooth functionality, 802.11-based technology, etc.) and/or according to a wired medium (e.g., universal serial bus (USB), etc.). Further discussion of the wearable device 12 is described below in association with FIG. 2.

The electronics device 14 may be embodied as a smartphone, mobile phone, cellular phone, pager, stand-alone image capture device (e.g., camera), laptop, workstation, smart glass (e.g., Google Glass™), virtual reality device, augmented reality device, smart watch, among other handheld and portable computing/communication devices. In some embodiments, the electronics device 14 is not necessarily readily portable or even portable. For instance, the electronics device 14 may be a home appliance, including a refrigerator, microwave, oven, pillbox, home monitor, stand-alone home virtual assistant device, one or more of which may be coupled to the computing system 20 via one or more networks (e.g., through the home Internet connection or telephony network), or a vehicle appliance (e.g., the automobile navigation system or communication system). In the depicted embodiment of FIG. 1, the electronics device 14 is a smartphone, though it should be appreciated that the electronics device 14 may take the form of other types of devices including those described above. Further discussion of the electronics device 14 is described below in association with FIG. 3, with smartphone and electronics device 14 used interchangeably hereinafter.

In one embodiment, the wearable device 12 or electronics device 14 individually comprise the full functionality of the proximity triggered sampling system. In some embodiments, the wearable device 12 and electronics device 14 collectively comprise the full functionality of the proximity triggered sampling system (e.g., the functionality of the proximity triggered sampling system is distributed among the two devices). In some embodiments, functionality of the proximity triggered sampling system is distributed among the wearable device 12 (or electronics device 14) and the computing system 20. In some embodiments, functionality of the proximity triggered sampling system is distributed among the wearable device 12, the electronics device 14, and the computing system 20. For instance, the wearable device 12 and/or the electronics device 14 may present electronic messages via a user interface and provide sensing functionality, yet rely on the remote computing systems 20 for processing and/or data (e.g., message) storage.

The cellular network 16 may include the necessary infrastructure to enable cellular communications by the electronics device 14 and optionally the wearable device 12. There are a number of different digital cellular technologies suitable for use in the cellular network 16, including: GSM, GPRS, CDMAOne, CDMA2000, Evolution-Data Optimized (EV-DO), EDGE, Universal Mobile Telecommunications System (UMTS), Digital Enhanced Cordless Telecommunications (DECT), Digital AMPS (IS-136/TDMA), and Integrated Digital Enhanced Network (iDEN), among others.

The wide area network 18 may comprise one or a plurality of networks that in whole or in part comprise the Internet. The electronics device 14 and optionally wearable device 12 may access one or more devices of the computing system 20 via the Internet 18, which may be further enabled through access to one or more networks including PSTN (Public Switched Telephone Networks), POTS, Integrated Services Digital Network (ISDN), Ethernet, Fiber, DSL/ADSL, among others.

The computing system 20 comprises one or more devices coupled to the wide area network 18, including one or more computing devices networked together, including an application server(s) and data storage. The computing system 20 may serve as a cloud computing environment (or other server network) for the electronics device 14 and/or wearable device 12, performing processing and data storage on behalf of (or in some embodiments, in addition to) the electronics devices 14 and/or wearable device 12. When embodied as a cloud service or services, the device(s) of the remote computing system 20 may comprise an internal cloud, an external cloud, a private cloud, or a public cloud (e.g., commercial cloud). For instance, a private cloud may be implemented using a variety of cloud systems including, for example, Eucalyptus Systems, VMWare vSphere®, or Microsoft® HyperV. A public cloud may include, for example, Amazon EC2®, Amazon Web Services®, Terremark®, Savvis®, or GoGrid®. Cloud-computing resources provided by these clouds may include, for example, storage resources (e.g., Storage Area Network (SAN), Network File System (NFS), and Amazon S3®), network resources (e.g., firewall, load-balancer, and proxy server), internal private resources, external private resources, secure public resources, infrastructure-as-a-services (IaaSs), platform-as-a-services (PaaSs), or software-as-a-services (SaaSs). The cloud architecture of the devices of the remote computing system 20 may be embodied according to one of a plurality of different configurations. For instance, if configured according to MICROSOFT AZURE™, roles are provided, which are discrete scalable components built with managed code. Worker roles are for generalized development, and may perform background processing for a web role. Web roles provide a web server and listen for and respond to web requests via an HTTP (hypertext transfer protocol) or HTTPS (HTTP secure) endpoint. VM roles are instantiated according to tenant defined configurations (e.g., resources, guest operating system). Operating system and VM updates are managed by the cloud. A web role and a worker role run in a VM role, which is a virtual machine under the control of the tenant. Storage and SQL services are available to be used by the roles. As with other clouds, the hardware and software environment or platform, including scaling, load balancing, etc., are handled by the cloud.

In some embodiments, the devices of the remote computing system 20 may be configured into multiple, logically-grouped servers (run on server devices), referred to as a server farm. The devices of the remote computing system 20 may be geographically dispersed, administered as a single entity, or distributed among a plurality of server farms, executing one or more applications on behalf of one or more of the electronic devices 14 and/or wearable device 12. The devices of the remote computing system 20 within each farm may be heterogeneous. One or more of the devices may operate according to one type of operating system platform (e.g., WINDOWS NT, manufactured by Microsoft Corp. of Redmond, Wash.), while one or more of the other devices may operate according to another type of operating system platform (e.g., Unix or Linux). The group of devices of the remote computing system 20 may be logically grouped as a farm that may be interconnected using a wide-area network (WAN) connection or medium-area network (MAN) connection. The devices of the remote computing system 20 may each be referred to as (and operate according to) a file server device, application server device, web server device, proxy server device, or gateway server device.

In one embodiment, the computing system 20 may comprise a web server that provides a web site that can be used by users to receive messages and/or input responses to a questionnaire, though other platforms may be used to enable user input or the receipt of electronic messages, including functionality that provides push notifications or device-run local applications. The computing system 20 may receive information (e.g., proximity data, physiological data, etc.) collected via one or more of the wearable device 12 or electronics device 14 and/or other devices or applications, store the received information in a user profile data structure (e.g., database) and/or other memory, process the information to determine a user state (e.g., psychological and/or physiological state of a user based in part on the proximity data and physiological data), and deliver electronic messages and/or solicit information from the user (e.g., mood questionnaire, etc.) via the electronics device 14 and/or wearable device 12. In some embodiments, the computing system 20 may change a data collection function characteristic(s), such as via sending instructions to the devices 12 and/or 14 to start/end measurements (e.g., heart rate measurements), track location (e.g., using GNSS functionality), change sampling rates, etc. Note that in some embodiments, all or at least a portion of the aforementioned computing system functionality may be implemented at the wearable device 12 and/or electronics device 14. The computing system 20 is programmed to handle the operations of one or more applications (e.g., health or wellness programs) implemented also on the wearable device 12 and/or electronics device 14 via the networks 16 and/or 18. For example, the computing system 20 processes user registration requests, user device activation requests, user information updating requests, data uploading requests, data synchronization requests, etc. The data received at the computing system 20 may include a plurality of measurements pertaining to sensed or determined parameters, for example, proximity data, body movements and activities, heart rate, respiration rate, blood pressure, body temperature, light and visual information, etc. and the corresponding context. Such measurements and/or information derived from the measurements may provide insight into the user state (e.g., the emotional, physical, or psychological state of the user), enabling the determination of opportune (meaningful) moments for change in message function characteristics and/or data collection function characteristics (e.g., change being activation, increase or decrease in sampling, etc.), which includes delivery of the messages and/or activation and/or change in data collection functionality. In some embodiments, the computing system 20 is configured to be a backend server for a health-related program or a health-related application implemented on the mobile devices. The functions of the computing system 20 described above are for illustrative purpose only. The present disclosure is not intended to be limiting. The computing system 20 may include one or more general computing server devices or dedicated computing server devices. The computing system 20 may be configured to provide backend support for a program developed by a specific manufacturer. However, the computing system 20 may also be configured to be interoperable across other server devices and generate information in a format that is compatible with other programs. In some embodiments, one or more of the functionality of the computing system 20 may be performed at the respective devices 12 and/or 14. Further discussion of the computing system 20 is described below in association with FIG. 4.

As one illustrative example of operations of an embodiment of a proximity triggered sampling system, in accordance with a client-server application (e.g., fitness or health related application, though other types of applications including those for business, rehab, training, instruction, etc. may be run), the wearable device 12 and/or electronics device 14 may be equipped with proximity sensing functionality (e.g., beacon technology) along with other sensing functionality (e.g., accelerometer, position detection, physiological monitoring, etc.). Social interactions between the user of the wearable device 12 and/or electronics device 14 and the users of other devices are monitored using the proximity sensing functionality (and in some embodiments, using other user data), including such social interaction characteristics as number of people involved in the interactions, the duration, location, characteristics of people involved, time (e.g., in a day) of the interaction, the duration between different interactions, the count of the interaction (e.g., is this the first, second, etc. interaction that the user had), changes observed in the proximity data during the interaction (e.g., people coming, people leaving), and in general, interactions between different interaction characteristics. For instance, the proximity triggered sampling system assesses interactions involving two one to one meetings (1-1, 1-1) and then a meeting with 30 people. It may be the case that due to the 1-1 meetings in the past, the user may react differently to the later meetings. In other words, certain embodiments of a proximity triggered sampling system consider historical data in assessments of the social interactions.

The proximity data, which includes the social interaction characteristics, and optionally other sensor data, may continually be communicated by the wearable device 12 and/or electronics device 14 to the computing system 20. Software in the computing system 20 uses the sensor data to predict when a user state of the user of the wearable device 12 and/or electronics device 14 is likely to change, and then changes message function characteristics (e.g., communicates a one-way or two-way message to the user, number and/or type of questions asked, etc.) and/or data collection function characteristics (e.g., control the beginning and end of a heart rate measurement, position tracking, etc.). In some embodiments, the application software to control functionality of the computing system 20 may be implemented entirely in the wearable device 12, the electronics device 14, and/or distributed among both devices 12 and 14 or all devices 12, 14, and device(s) of the computing system 20. As indicated above, the wearable device 12, electronic device 14, and the computing system 20 may operate under a health and wellness program that monitors the performance and/or progress of the user under the program and provides electronic messaging to the user that has an optimal impact on the user (e.g., via the pushing of appropriate one-way communication messages for the current context of the user, pushing two-way messages to ascertain an emotional state of the user, or collecting data). For instance, the user input data can be mined together with the heart rate (HR) data, for determining later sampling moments. In some embodiments, the collected data may be used to calculate an indicator of the difference between subjective (e.g. user input based emotions) and objective measurements (e.g. HR based emotions) and these can be used to tailor one or more sampling characteristics. In some applications, including rehabilitation, it may be desirable to gather high fidelity data that would enable calculating of the additional parameters, such as heart rate variability (HRV). HRV requires that the heart rate signal be of higher quality, with individual cycle peaks being detectable, and for at least a certain duration (e.g., for a suggested duration equal to a minimum of 5 minutes.) For people suffering from anxiety, stress or mood swings, it may be very relevant to have access to HRV data. In cases where there are physical limitations in the devices (e.g. limited storage, memory, battery), it is beneficial to activate and deactivate the HR only at certain moments to conserve resources.

Attention is now directed to FIG. 2, which illustrates an example wearable device 12 in which all or a portion of the functionality of a proximity triggered sampling system may be implemented. That is, FIG. 2 illustrates an example architecture (e.g., hardware and software) for the example wearable device 12. It should be appreciated by one having ordinary skill in the art in the context of the present disclosure that the architecture of the wearable device 12 depicted in FIG. 2 is but one example, and that in some embodiments, additional, fewer, and/or different components may be used to achieve similar and/or additional functionality. In one embodiment, the wearable device 12 comprises a plurality of sensors 22 (e.g., 22A-22N), one or more signal conditioning circuits 24 (e.g., SIG COND CKT 24A-SIG COND CKT 24N) coupled respectively to the sensors 22, and a processing circuit 26 (PROCES CKT) that receives the conditioned signals from the signal conditioning circuits 24. In one embodiment, the processing circuit 26 comprises an analog-to-digital converter (ADC), a digital-to-analog converter (DAC), a microcontroller unit (MCU), a digital signal processor (DSP), and memory (MEM) 28. In some embodiments, the processing circuit 26 may comprise fewer or additional components than those depicted in FIG. 2. For instance, in one embodiment, the processing circuit 26 may consist entirely of the microcontroller. In some embodiments, the processing circuit 26 may include the signal conditioning circuits 24. The memory 28 comprises an operating system (OS) and application software (ASW) 30, which may be used to execute a particular health and wellness program for a user (or in some embodiments, business program, rehabilitation program, training program, etc.). In the depicted embodiment, the application software 30 comprises a sensor measurement module (SMM) 32, a prediction module (PM) 34, an interface module (IM) 36, and a communications module (CM) 38. In some embodiments, additional modules used to achieve the disclosed functionality of a proximity triggered sampling system, among other functionality, may be included, or one or more of the modules 32-38 may be separate from the application software 30. In some embodiments, fewer than all of the modules 32-38 may be used in the wearable device 12, such as in embodiments where the wearable device 12 merely provides sensor functionality for communication of sensor data to one or more other devices.

The sensor measurement module 32 in cooperation with the sensors 22 collectively comprise a data collection function for the wearable device 12. In one embodiment, the sensor measurement module 32 comprises executable code (instructions) to process the signals (and associated data) measured by the sensors 22 and record and/or derive physiological parameters, such as heart rate, blood pressure, respiration, perspiration, etc. and movement and/or location data. In some embodiments, the sensors 22 comprise beacon technology (e.g., using Bluetooth Low Energy, such as found in iBeacon technology), where the beacons provide proximity data for use by the prediction module 34 (along with other data in some embodiments). In some embodiments, the sensor measurement module 32 may comprise location positioning software (e.g., in cooperation with GNSS receiver functionality included among the sensors 22). The measured information (or information derived from the measured information) may be used in some embodiments of a proximity triggered sampling system to provide context about a user's psychological and/or physiological state, as used by the prediction module 34 to predict a moment in time when a change state of a user is likely.

The prediction module 34, explained further below, receives data (e.g., proximity data, physiological data, and optionally other contextual data) and repeatedly generates proximity graphs in real time. By monitoring the proximity data, changes in social interactions with the user may be determined, enabling the prediction module 34 to predict when the state of a user is likely to change and selecting those moments to change communication function characteristics and/or data collection function characteristics. One result of prediction can be to initiate a communication with a user (e.g., present a message) and/or change a type (e.g., content) and/or frequency or timing of the message. The message can be presented as a one-way message (no user response required), or as a two-way message wherein an initiation of a dialog takes place where some user input/response is solicited or expected. Another result of the prediction may be to change data collection function characteristics of a user device. For example, a sensor 22 in the wearable device 12 (e.g. for HR measurements) may be activated, or position detection tracking functionality (e.g., GNSS functionality) may be activated, and/or a change in the setting of the device 12 (e.g. increase of the sampling frequency of accelerometer and HR sensor) may be realized. Another example for a result of the prediction is the storage of parameters in a database. For instance, by storing the parameters, the parameters may be processed and used to improve the prediction algorithms. In other words, in some embodiments, the proximity triggered sampling system functions as a dynamic system that learns with every new set of data. When it is detected that the user's state may have changed, it is important to have the data stored. In one embodiment, the proximity triggered sampling system may process and display the sensor data in real-time, but only start storing the data in cases and periods where the users state change has been predicted, and the sampling characteristics adapted. In one embodiment, the proximity triggered sampling system may store data only when the user has responded to the initiated communication, enabling a valuable result that the data may be labelled. Having good, well-labeled data is beneficial, and thus by storing data when the user has responded, the user's responses can be used as labels for the data (which later may be used in the training of classification algorithms). One or any combination of these results may be implemented in the wearable device 12 (or other devices 14 or device(s) of the computing system 20 in which the prediction module 34 is used). In some embodiments, the result of the prediction is that nothing further is done (no change in operations).

The interface module 36 comprises executable code (instructions) to enable the presentation of electronic messages to the user at a moment in time that is meaningful (corresponding to the time when the user state is likely to change). In some embodiments, the interface module 36 may comprise functionality to enable the input (via voice or typed entry or gestures of different body parts such as hands, head, etc.) of user input, including in response to questions presented in the electronic messages. In one embodiment, the interface module 36 generates a graphical user interface (GUI) on a display screen of the wearable device 12, and/or provides other functionality, including in some embodiments virtual or augmented reality type functionality.

The communications module 38 comprises executable code (instructions) to enable a communications circuit 40 of the wearable device 12 to operate according to one or more of a plurality of different communication technologies (e.g., NFC, Bluetooth, Zigbee, etc.). In some embodiments, the communications module 38 provides control for any beacons delivered and/or detected by at least one of the sensors 22. In some embodiments, the communications module 38 may perform beacon transmission and reception, though still referred to herein as a sensing function. For purposes of illustration, the communications module 38 is described herein as providing for control of communications with the electronics device 14 and/or the computing system 20 (FIG. 1). In an embodiment where the prediction functionality is performed at the electronics device 14 or the computing system 20, the communications module 38, in cooperation with the communications circuit 40, may provide for the transmission of raw sensor data and/or the derived information from the sensor data to the electronics device 14 for processing by the electronics device 14, or to the computing system 20 (directly via the cellular network 16 and/or Internet or via the electronics device 14) for processing at the computing system 20. The communications module 38, in cooperation with the communications circuit 40, may receive any messages (or instructions to activate and/or increase/decrease data collection function characteristics) from the electronics device 14 or the computing system 20 for presentation to the user at the wearable device 12. In some embodiments, the presentation of the messages may occur at the electronics device 14. In some embodiments, the communications module 38 may also include browser software in some embodiments to enable Internet connectivity, and may also be used to access certain services, such as mapping/place location services, which may be used to determine a context for the sensor data. These services may be used in some embodiments of a proximity triggered sampling system, and in some instances, may not be used. In some embodiments, the location services may be performed by a client-server application running on the electronics device 14 and a device of the remote computing system 20. Further, some embodiments of the wearable device 12 may comprise only a portion of the functionality of an embodiment of a proximity triggered sampling system.

As indicated above, in one embodiment, the processing circuit 26 is coupled to the communications circuit 40. The communications circuit 40 serves to enable wireless communications between the wearable device 12 and other devices, including the electronics device 14 and/or in some embodiments, device(s) of the computing system 20, among other devices. The communications circuit 40 is depicted as a Bluetooth circuit, though not limited to this transceiver configuration. For instance, in some embodiments, the communications circuit 40 may be embodied as any one or a combination of an NFC circuit, Wi-Fi circuit, transceiver circuitry based on Zigbee, 802.11, GSM, LTE, CDMA, WCDMA, among others such as optical or ultrasonic based technologies.

The processing circuit 26 is further coupled to input/output (I/O) devices or peripherals, including an input interface 42 (INPUT) and the output interface 44 (OUT). Note that in some embodiments, functionality for one or more of the aforementioned circuits and/or software may be combined into fewer components/modules, or in some embodiments, further distributed among additional components/modules or devices. For instance, the processing circuit 26 may be packaged as an integrated circuit that includes the microcontroller (microcontroller unit or MCU), the DSP, and memory 28, whereas the ADC and DAC may be packaged as a separate integrated circuit coupled to the processing circuit 26. In some embodiments, one or more of the functionality for the above-listed components may be combined, such as functionality of the DSP performed by the microcontroller.

The sensors 22 are selected to perform detection and measurement of a plurality of physiological and behavioral parameters. For instance, typical physiological parameters include heart rate, heart rate variability, heart rate recovery, blood flow rate, activity level, muscle activity (e.g., movement of limbs, repetitive movement, core movement, body orientation/position, power, speed, acceleration, etc.), muscle tension, blood volume, blood pressure, blood oxygen saturation, respiratory rate, perspiration, skin temperature, electrodermal activity (skin conductance response), body weight, and body composition (e.g., body mass index or BMI), articulator movements (especially during speech). Typical behavioral parameters or activities including walking, running, cycling, and/or other activities, including shopping, walking a dog, working in the garden, sports activities, browsing internet, watching TV, typing, etc.). At least one of the sensors 22 may be embodied as movement and/or pressure detecting sensors, including inertial sensors (e.g., gyroscopes, single or multi-axis accelerometers, such as those using piezoelectric, piezoresistive or capacitive technology in a microelectromechanical system (MEMS) infrastructure for sensing movement). In some embodiments, at least one of the sensors 22 may include GNSS sensors, including a GPS receiver to facilitate determinations of distance, speed, acceleration, location, altitude, etc. (e.g., location data, or generally, sensing movement), in addition to or in lieu of the accelerometer/gyroscope and/or indoor tracking (e.g., Wi-Fi, coded-light based technology, etc.). In some embodiments, GNSS sensors (e.g., GNSS receiver and antenna(s)) may be included in the electronics device 14 in addition to, or in lieu of, those residing in the wearable device 12. The sensors 22 may also include flex and/or force sensors (e.g., using variable resistance), electromyographic sensors, electrocardiographic sensors (e.g., EKG, ECG), magnetic sensors, photoplethysmographic (PPG) sensors, bio-impedance sensors, infrared proximity sensors, acoustic/ultrasonic/audio sensors, a strain gauge, galvanic skin/sweat sensors, pH sensors, temperature sensors, pressure sensors, and photocells. The sensors 22 may include other and/or additional types of sensors for the detection of environmental parameters and/or conditions, for instance, barometric pressure, humidity, outdoor temperature, pollution, noise level, etc. One or more of these sensed environmental parameters/conditions may be influential in the determination of the state of the user. In some embodiments, the sensors 22 include proximity sensors (e.g., iBeacon® and/or other indoor/outdoor positioning functionality, including those based on Wi-Fi or dedicated sensors), that are used to determine proximity of the wearable device 12 to other devices that also are equipped with beacon or proximity sensing technology. In some embodiments, GNSS functionality and/or the beacon functionality may be achieved via the communications circuit 40 or other circuits coupled to the processing circuit 26.

The signal conditioning circuits 24 include amplifiers and filters, among other signal conditioning components, to condition the sensed signals including data corresponding to the sensed physiological parameters and/or location signals before further processing is implemented at the processing circuit 26. Though depicted in FIG. 2 as respectively associated with each sensor 22, in some embodiments, fewer signal conditioning circuits 24 may be used (e.g., shared for more than one sensor 22). In some embodiments, the signal conditioning circuits 24 (or functionality thereof) may be incorporated elsewhere, such as in the circuitry of the respective sensors 22 or in the processing circuit 26 (or in components residing therein). Further, although described above as involving unidirectional signal flow (e.g., from the sensor 22 to the signal conditioning circuit 24), in some embodiments, signal flow may be bi-directional. For instance, in the case of optical measurements, the microcontroller may cause an optical signal to be emitted from a light source (e.g., light emitting diode(s) or LED(s)) in or coupled to the circuitry of the sensor 22, with the sensor 22 (e.g., photocell) receiving the reflected/refracted signals. In the case of beacon technology, beacons may be transmitted from and received by at least one of the sensors 22.

The communications circuit 40 is managed and controlled by the processing circuit 26 (e.g., executing the communications module 38). The communications circuit 40 is used to wirelessly interface with the electronics device 14 (FIG. 3) and/or in some embodiments, one or more devices of the computing system 20. In one embodiment, the communications circuit 40 may be configured as a Bluetooth transceiver, though in some embodiments, other and/or additional technologies may be used, such as Wi-Fi, GSM, LTE, CDMA and its derivatives, Zigbee, NFC, among others. In the embodiment depicted in FIG. 2, the communications circuit 40 comprises a transmitter circuit (TX CKT), a switch (SW), an antenna, a receiver circuit (RX CKT), a mixing circuit (MIX), and a frequency hopping controller (HOP CTL). The transmitter circuit and the receiver circuit comprise components suitable for providing respective transmission and reception of an RF signal, including a modulator/demodulator, filters, and amplifiers. In some embodiments, demodulation/modulation and/or filtering may be performed in part or in whole by the DSP. The switch switches between receiving and transmitting modes. The mixing circuit may be embodied as a frequency synthesizer and frequency mixers, as controlled by the processing circuit 26. The frequency hopping controller controls the hopping frequency of a transmitted signal based on feedback from a modulator of the transmitter circuit. In some embodiments, functionality for the frequency hopping controller may be implemented by the microcontroller or DSP. Control for the communications circuit 40 may be implemented by the microcontroller, the DSP, or a combination of both. In some embodiments, the communications circuit 40 may have its own dedicated controller that is supervised and/or managed by the microcontroller.

In one example operation for the communications circuit 40, a signal (e.g., at 2.4 GHz) may be received at the antenna and directed by the switch to the receiver circuit. The receiver circuit, in cooperation with the mixing circuit, converts the received signal into an intermediate frequency (IF) signal under frequency hopping control attributed by the frequency hopping controller and then to baseband for further processing by the ADC. On the transmitting side, the baseband signal (e.g., from the DAC of the processing circuit 26) is converted to an IF signal and then RF by the transmitter circuit operating in cooperation with the mixing circuit, with the RF signal passed through the switch and emitted from the antenna under frequency hopping control provided by the frequency hopping controller. The modulator and demodulator of the transmitter and receiver circuits may perform frequency shift keying (FSK) type modulation/demodulation, though not limited to this type of modulation/demodulation, which enables the conversion between IF and baseband. In some embodiments, demodulation/modulation and/or filtering may be performed in part or in whole by the DSP. The memory 28 stores the communications module 38, which when executed by the microcontroller, controls the Bluetooth (and/or other protocols) transmission/reception.

Though the communications circuit 40 is depicted as an IF-type transceiver, in some embodiments, a direct conversion architecture may be implemented. As noted above, the communications circuit 40 may be embodied according to other and/or additional transceiver technologies.

The processing circuit 26 is depicted in FIG. 2 as including the ADC and DAC. For sensing functionality, the ADC converts the conditioned signal from the signal conditioning circuit 24 and digitizes the signal for further processing by the microcontroller and/or DSP. The ADC may also be used to convert analogs inputs that are received via the input interface 42 to a digital format for further processing by the microcontroller. The ADC may also be used in baseband processing of signals received via the communications circuit 40. The DAC converts digital information to analog information. Its role for sensing functionality may be to control the emission of signals, such as optical signals or acoustic signals, from the sensors 22. The DAC may further be used to cause the output of analog signals from the output interface 44. Also, the DAC may be used to convert the digital information and/or instructions from the microcontroller and/or DSP to analog signals that are fed to the transmitter circuit. In some embodiments, additional conversion circuits may be used.

The microcontroller and the DSP provide processing functionality for the wearable device 12. In some embodiments, functionality of both processors may be combined into a single processor, or further distributed among additional processors. The DSP provides for specialized digital signal processing, and enables an offloading of processing load from the microcontroller. The DSP may be embodied in specialized integrated circuit(s) or as field programmable gate arrays (FPGAs). In one embodiment, the DSP comprises a pipelined architecture, which comprises a central processing unit (CPU), plural circular buffers and separate program and data memories according to a Harvard architecture. The DSP further comprises dual busses, enabling concurrent instruction and data fetches. The DSP may also comprise an instruction cache and I/O controller, such as those found in Analog Devices SHARC® DSPs, though other manufacturers of DSPs may be used (e.g., Freescale multi-core MSC81xx family, Texas Instruments C6000 series, etc.). The DSP is generally utilized for math manipulations using registers and math components that may include a multiplier, arithmetic logic unit (ALU, which performs addition, subtraction, absolute value, logical operations, conversion between fixed and floating point units, etc.), and a barrel shifter. The ability of the DSP to implement fast multiply-accumulates (MACs) enables efficient execution of Fast Fourier Transforms (FFTs) and Finite Impulse Response (FIR) filtering. Some or all of the DSP functions may be performed by the microcontroller. The DSP generally serves an encoding and decoding function in the wearable device 12. For instance, encoding functionality may involve encoding commands or data corresponding to transfer of information to the electronics device 14 (or a device of the computing system 20 in some embodiments). Also, decoding functionality may involve decoding the information received from the sensors 22 (e.g., after processing by the ADC).

The microcontroller comprises a hardware device for executing software/firmware, particularly that stored in memory 28. The microcontroller can be any custom made or commercially available processor, a central processing unit (CPU), a semiconductor based microprocessor (in the form of a microchip or chip set), a macroprocessor, or generally any device for executing software instructions. Examples of suitable commercially available microprocessors include Intel's® Itanium® and Atom® microprocessors, to name a few non-limiting examples. The microcontroller provides for management and control of the wearable device 12, including determining physiological parameters or location coordinates or other contextual data based on the sensors 22, and for enabling communication with the electronics device 14 (and/or a device of the computing system 20 in some embodiments).

The memory 28 can include any one or a combination of volatile memory elements (e.g., random access memory (RAM, such as DRAM, SRAM, SDRAM, etc.)) and non-volatile memory elements (e.g., ROM, Flash, solid state, EPROM, EEPROM, etc.). Moreover, the memory 28 may incorporate electronic, magnetic, and/or other types of storage media.

The software in memory 28 may include one or more separate programs, each of which comprises an ordered listing of executable instructions for implementing logical functions. In the example of FIG. 2, the software in the memory 28 includes a suitable operating system and the application software 30, which in one embodiment, runs a health and wellness program (though programs for other services, including business, training, etc. may be used) that includes a plurality of software modules 32-38 for implementing certain embodiments of a proximity triggered sampling system based on the output from the sensors 22 and optionally other inputted data. The raw data from the sensors 22 may be used by algorithms of the sensor measurement module 32 to determine various environmental, physiological and/or behavioral measures (e.g., heart rate, biomechanics, such as swinging of the arms), and may also be used to derive other parameters, such as energy expenditure, heart rate recovery, calories, aerobic capacity (e.g., VO2 max, etc.), among other derived measures of physical performance. In some embodiments, these derived parameters may be computed externally (e.g., at the electronics devices 14 or one or more devices of the computing system 20) in lieu of, or in addition to, the computations performed local to the wearable device 12.

The operating system essentially controls the execution of computer programs, such as the application software 30 and associated modules 32-38, and provides scheduling, input-output control, file and data management, memory management, and communication control and related services. The memory 28 may also include user data, including weight, height, age, gender, goals, body mass index (BMI) that are used by the microcontroller executing the executable code of the algorithms to accurately interpret the measured proximity data, physiological, psychological, and/or behavioral data. The user data may also include historical data relating past recorded data to prior contexts. In some embodiments, user data may be stored elsewhere (e.g., at the electronics device 14 and/or a device of the remote computing system 20). The memory may also store proximity graphs generated repeatedly by the prediction module 34 for analysis.

The software in memory 28 comprises a source program, executable program (object code), script, or any other entity comprising a set of instructions to be performed. When a source program, then the program may be translated via a compiler, assembler, interpreter, or the like, so as to operate properly in connection with the operating system. Furthermore, the software can be written as (a) an object oriented programming language, which has classes of data and methods, or (b) a procedure programming language, which has routines, subroutines, and/or functions, for example but not limited to, C, C++, Python, Java, among others. The software may be embodied in a computer program product, which may be a non-transitory computer readable medium or other medium.

The input interface(s) 42 comprises one or more interfaces (e.g., including a user interface) for entry of user input, such as a button or microphone or sensor (e.g., to detect user input) or touch-type display screen. In some embodiments, the input interface 42 may serve as a communications port for downloaded information to the wearable device 12 (such as via a wired connection). The output interface(s) 44 comprises one or more interfaces for the presentation or transfer of data, including a user interface (e.g., display screen presenting a graphical user interface, virtual or augmented reality interface, etc.) or communications interface for the transfer (e.g., wired) of information stored in the memory, or to enable one or more feedback devices, such as lighting devices (e.g., LEDs), audio devices (e.g., tone generator and speaker), and/or tactile feedback devices (e.g., vibratory motor) and/or electrical feedback devices. For instance, the output interface 44 may be used to present the electronic messages to the user in some embodiments. In some embodiments, at least some of the functionality of the input and output interfaces 42 and 44, respectively, may be combined, including being embodied at least in part as a touch-type display screen for the entry of input and/or presentation of messages, among other data.

Figure 3:
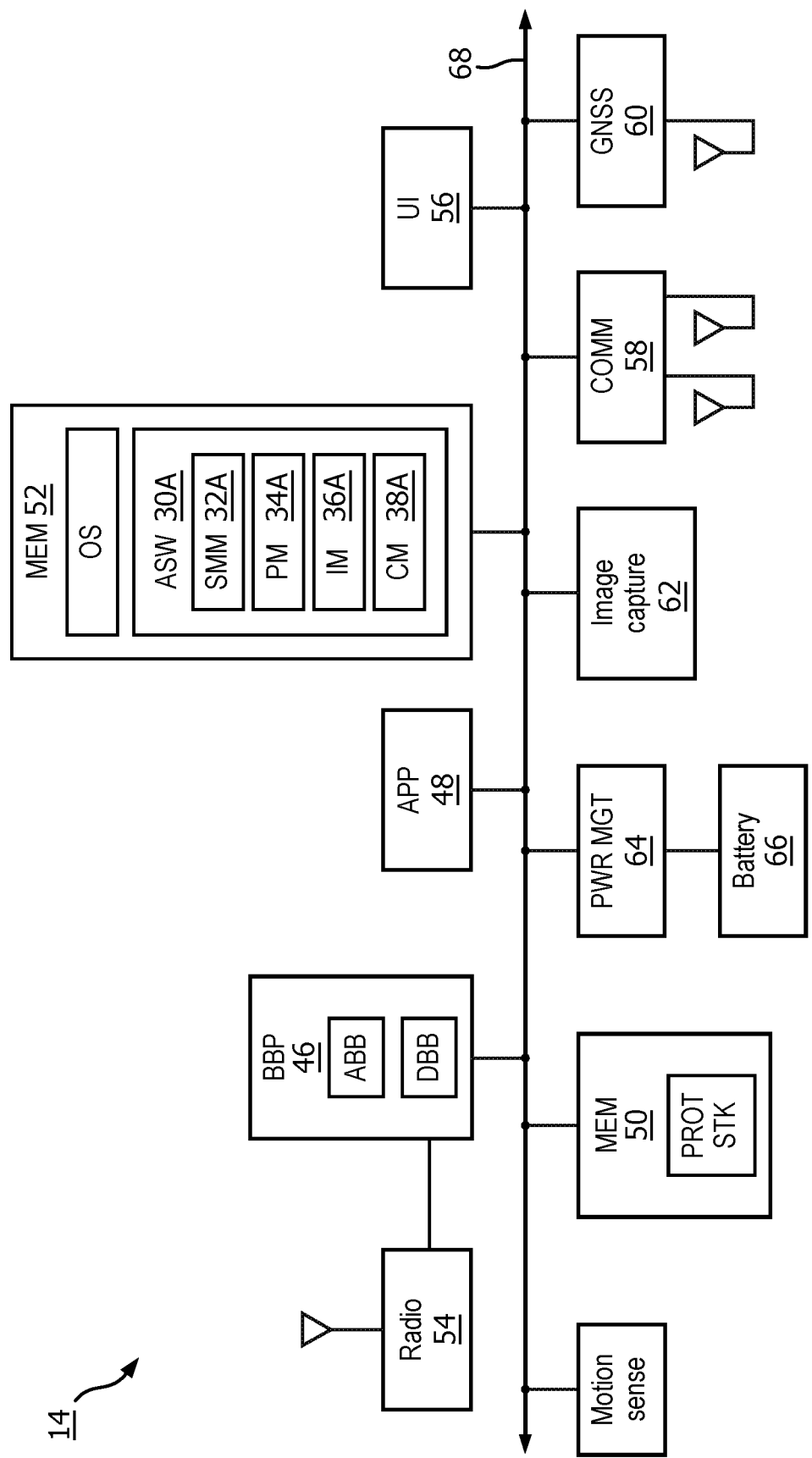
FIG. 3 is a schematic diagram that illustrates an example electronics device in which all or a portion of the functionality of a proximity triggered sampling system may be implemented, in accordance with an embodiment of the invention.

Referring now to FIG. 3, shown is an example electronics device 14 in which all or a portion of the functionality of a proximity triggered sampling system may be implemented. In the depicted example, the electronics device 14 is embodied as a smartphone (hereinafter, referred to as smartphone 14), though in some embodiments, other types of devices may be used, including a workstation, laptop, notebook, tablet, home or auto appliance, etc. It should be appreciated by one having ordinary skill in the art that the logical block diagram depicted in FIG. 3 and described below is one example, and that other designs may be used in some embodiments. The application software 30A, which may include functionality to run a health and wellness (e.g., fitness) program, among other programs, comprises a plurality of software modules (e.g., executable code/instructions) including the sensor measurement module 32A, prediction module 34A, interface module 36A, and communications module (CM) 38A, all of which are similar to like-named modules for the application software 30 of the wearable device 12, and omitted here for brevity except where noted below. In some embodiments, the application software 30A may include additional software modules or fewer software modules/functionality. For instance, as described above, in some embodiments, the application software 30A may comprise all of the functionality of the proximity triggered sampling system (e.g., functionality for sensor measurement, prediction of a moment in time when a user state is likely to change, and the change in message function characteristics and/or data collection function characteristics), or a subset thereof in some embodiments. The smartphone 14 comprises at least two different processors, including a baseband processor (BBP) 46 and an application processor (APP) 48. As is known, the baseband processor 46 primarily handles baseband communication-related tasks and the application processor 48 generally handles inputs and outputs and all applications other than those directly related to baseband processing. The baseband processor 46 comprises a dedicated processor for deploying functionality associated with a protocol stack (PROT STK), such as a GSM (Global System for Mobile communications) protocol stack, among other functions. The application processor 48 comprises a multi-core processor for running applications, including all or a portion of the application software 30A and its corresponding component modules 32A-38A. The baseband processor 46 and application processor 48 have respective associated memory (e.g., MEM) 50, 52, including random access memory (RAM), Flash memory, etc., and peripherals, and a running clock. Note that, though depicted as residing in memory 52, all or a portion of the modules 32A-38A of the application software 30A may be stored in memory 50, distributed among memory 50, 52, or reside in other memory.

More particularly, the baseband processor 46 may deploy functionality of the protocol stack to enable the smartphone 14 to access one or a plurality of wireless network technologies, including WCDMA (Wideband Code Division Multiple Access), CDMA (Code Division Multiple Access), EDGE (Enhanced Data Rates for GSM Evolution), GPRS (General Packet Radio Service), Zigbee (e.g., based on IEEE 802.15.4), Bluetooth, Wi-Fi (Wireless Fidelity, such as based on IEEE 802.11), and/or LTE (Long Term Evolution), among variations thereof and/or other telecommunication protocols, standards, and/or specifications. The baseband processor 46 manages radio communications and control functions, including signal modulation, radio frequency shifting, and encoding. The baseband processor 46 comprises, or may be coupled to, a radio (e.g., RF front end) 54 and/or a GSM modem, and analog and digital baseband circuitry (ABB, DBB, respectively in FIG. 3). The radio 54 comprises one or more antennas, a transceiver, and a power amplifier to enable the receiving and transmitting of signals of a plurality of different frequencies, enabling access to the cellular network 16 (FIG. 1). In embodiments where functionality of the proximity triggered sampling system is distributed among the electronics device 14 and the computing system 20 (and optionally the wearable device 12), the radio 54 enables the communication of proximity data (from its integrated beacon technology or other proximity detection functionality) and any other data (acquired via sensing functionality of the electronics device 14 and or relayed from inputs from a wearable device 12), and the receipt of messages (e.g., from the computing system 20) and/or instructions to activate or increase data collection functionality (at the electronics device 14 or for relaying to the wearable device 12). The analog baseband circuitry is coupled to the radio 54 and provides an interface between the analog and digital domains of the GSM modem. The analog baseband circuitry comprises circuitry including an analog-to-digital converter (ADC) and digital-to-analog converter (DAC), as well as control and power management/distribution components and an audio codec to process analog and/or digital signals received indirectly via the application processor 48 or directly from a smartphone user interface (UI) 56 (e.g., microphone, earpiece, ring tone, vibrator circuits, touch-screen, etc.). The microphone may be one mechanism for detecting interactions with a user (similar with any microphone functionality of the wearable device). The ADC digitizes any analog signals for processing by the digital baseband circuitry. The digital baseband circuitry deploys the functionality of one or more levels of the GSM protocol stack (e.g., Layer 1, Layer 2, etc.), and comprises a microcontroller (e.g., microcontroller unit or MCU, also referred to herein as a processor) and a digital signal processor (DSP, also referred to herein as a processor) that communicate over a shared memory interface (the memory comprising data and control information and parameters that instruct the actions to be taken on the data processed by the application processor 48). The MCU may be embodied as a RISC (reduced instruction set computer) machine that runs a real-time operating system (RTIOS), with cores having a plurality of peripherals (e.g., circuitry packaged as integrated circuits) such as RTC (real-time clock), SPI (serial peripheral interface), I2C (inter-integrated circuit), UARTs (Universal Asynchronous Receiver/Transmitter), devices based on IrDA (Infrared Data Association), SD/MMC (Secure Digital/Multimedia Cards) card controller, keypad scan controller, and USB devices, GPRS crypto module, TDMA (Time Division Multiple Access), smart card reader interface (e.g., for the one or more SIM (Subscriber Identity Module) cards), timers, and among others. For receive-side functionality, the MCU instructs the DSP to receive, for instance, in-phase/quadrature (I/Q) samples from the analog baseband circuitry and perform detection, demodulation, and decoding with reporting back to the MCU. For transmit-side functionality, the MCU presents transmittable data and auxiliary information to the DSP, which encodes the data and provides to the analog baseband circuitry (e.g., converted to analog signals by the DAC).

The application processor 48 operates under control of an operating system (OS) that enables the implementation of a plurality of user applications, including the application software 30A (e.g., a health and wellness program, though others may be used). The application processor 48 may be embodied as a System on a Chip (SOC), and supports a plurality of multimedia related features including web browsing functionality of the communications module 38A to access one or more computing devices of the computing system 20 (FIG. 4) that are coupled to the Internet. For instance, the application processor 48 may execute the communications module 38A (e.g., middleware, such as a browser with or operable in association with one or more application program interfaces (APIs)) to enable access to a cloud computing framework or other networks to provide remote data access/storage/processing, and through cooperation with an embedded operating system, access to calendars, location services, reminders, etc. For instance, in some embodiments, the proximity triggered sampling system may operate using cloud computing, where the processing of data received (indirectly via the smartphone 14 or directly) from the wearable device 12 and context data (e.g., location data, environmental data, etc.) and user inputted data and other data received from the smartphone 14, including proximity data, motion sense, accelerations, speed of travel, imaging, radio tag information (e.g., RFID), etc.), may be achieved by one or more devices of the computing system 20, and messaging and/or data collection functionality may be implemented at the electronics device 14 (and/or the wearable device 12). The application processor 48 generally comprises a processor core (Advanced RISC Machine or ARM), and further comprises or may be coupled to multimedia modules (for decoding/encoding pictures, video, and/or audio), a graphics processing unit (GPU), communications interface (COMM) 58, and device interfaces. In one embodiment, the communications interfaces 58 may include wireless interfaces, including a Bluetooth (BT) (and/or Zigbee in some embodiments) module that enable wireless communication with an electronics device, including the wearable device 12, other electronics devices, and a Wi-Fi module for interfacing with a local 802.11 network, according to corresponding software in the communications module 38A. The communications interface 58 may further comprise beacon technology to acquire proximity data. The application processor 48 further comprises, or in the depicted embodiment, is coupled to, a global navigation satellite systems (GNSS) transceiver or receiver (GNSS) 60 for enabling access to a satellite network to, for instance, provide coordinate location services. In some embodiments, the GNSS receiver 60, in association with GNSS functionality (e.g., the sensor measurement module 32A) in the application software 30A, collects contextual data (time and location data, including location coordinates and altitude), and provides a time stamp to the information provided internally or to a device or devices of the computing system 20 in some embodiments. Note that, though described as a GNSS receiver 60, other indoor/outdoor positioning systems may be used, including those based on triangulation of cellular network signals and/or Wi-Fi. In some embodiments, the sensor measurement module 32A of the application software 30A may compute speed of movement of the smartphone 14 (and/or other sensor data, including acceleration data) for provision of the contextual information (e.g., meta information) internally or to the remote computing system 20. For instance, the application software 30A may also collect information about the means of ambulation, where the GNSS data (which may include time coordinates) may be used by the application software 30A to determine speed of travel, which may indicate whether the user is moving within a vehicle, on a bicycle, or walking or running. In some embodiments, other and/or additional data may be used to assess the type of activity, including environmental data (e.g., humidity, pollution, temperature, etc.), physiological data (e.g., heart rate, respiration rate, galvanic skin response, etc.) and/or behavioral data, enabling for instance, a determination of the emotional and/or psychological state of the user by the prediction module 34A.

The device interfaces coupled to the application processor 48 may include the user interface 56, including a display screen. The display screen, in some embodiments similar to a display screen of the wearable device user interface, may be embodied in one of several available technologies, including LCD or Liquid Crystal Display (or variants thereof, such as Thin Film Transistor (TFT) LCD, In Plane Switching (IPS) LCD)), light-emitting diode (LED)-based technology, such as organic LED (OLED), Active-Matrix OLED (AMOLED), retina or haptic-based technology, or virtual/augmented reality technology. For instance, the interface module 36A may use the display screen to present web pages, personalized electronic messages, and/or other documents or data received from the computing system 20 and/or the display screen may be used to present information (e.g., personalized electronic messages) in graphical user interfaces (GUIs) rendered locally in association with the interface module 36A. Other user interfaces 56 may include a keypad, microphone, speaker, ear piece connector, I/O interfaces (e.g., USB (Universal Serial Bus), SD/MMC card), among other peripherals. Also coupled to the application processor 48 is an image capture device (IMAGE CAPTURE) 62. The image capture device 62 comprises an optical sensor (e.g., a charged coupled device (CCD) or a complementary metal-oxide semiconductor (CMOS) optical sensor). The image capture device 62 may be used to detect various physiological parameters of a user, including blood pressure based on remote photoplethysmography (PPG). Also included is a power management device 64 that controls and manages operations of a battery 66. The components described above and/or depicted in FIG. 3 share data over one or more busses, and in the depicted example, via data bus 68. It should be appreciated by one having ordinary skill in the art, in the context of the present disclosure, that variations to the above may be deployed in some embodiments to achieve similar functionality.

In the depicted embodiment, the application processor 48 runs the application software 30A, which in one embodiment, includes a plurality of software modules (e.g., executable code/instructions) including the sensor measurement module (SMM) 32A, a prediction module (PM) 34A, an interface module (IM) 36A, and a communications module (CM) 38A. In some embodiments, GNSS (or like) functionality may be incorporated in the communication module 38A or in a separate position determining module, wherein the GNSS functionality operates with the GNSS receiver 60 to interpret the data to provide a location and time of the user activity. The GNSS functionality of the application software 30A provides location coordinates (and a corresponding time) of the user based on the GNSS receiver input. In some embodiments, the GNSS functionality of the application software 30A cooperates with local or external location servicing services, wherein the GNSS functionality of the application software 30A receives descriptive information and converts the information to latitude and longitude coordinates. In one embodiment, the communication module 38A, in conjunction with the communications interface 58, enables the receipt from, and/or communication of data to, the wearable device 12 (FIG. 2), and also the transmission of beacons to one or more other devices, and the receipt of beacons from one or more other devices. From the receipt of beacons from other devices, the application software 30A (e.g., the prediction module 34A) can determine proximity graphs and determine a likelihood of a user state change (and hence meaningful moments) to communicate a message to the user and/or activate (or increase) data collection functionality characteristics as explained further below. The communications module 38A may enable operations according to any one or more of a variety of technologies, including BT, NFC, RFID, etc. The communications module 38A further includes network interfacing software, including browser software, to access the Internet (and in particular, one or more devices of the computing system 20). The interface module 36A may render a GUI on the display screen (e.g., user interface 56) for the presentation of messages based on the predicted meaningful moment (user state change) by the prediction module 34A, and/or present a message audibly (e.g., according to speaker functionality of the electronics device 14). The interface module 36A, through presentation of the messages, may also enable via the GUI input by the user in response to questions presented in the message. In some embodiments, one or more of the software modules and/or corresponding functionality of the application software 30A may be further distributed among additional software modules, or in some embodiments, performed at other devices in addition to, or in lieu of, implementation at the smartphone 14. The sensor measurement module 32A comprises executable code to process the signals (and associated data) measured by the sensors (of the wearable device 12 as communicated to the smartphone 14, or based on sensors integrated within the smartphone 14) and record and/or derive physiological parameters, such as heart rate, blood pressure, respiration, perspiration, etc. The sensor measurement module 32A may activate a data collection function in the electronics device 14, including heart rate monitoring (e.g., via the image capture device 62), location tracking (via the GNSS functionality), audio recording functionality, motion sense functionality (e.g., accelerometer to sense appendage or torso movement), environmental parameter/condition monitoring, at the moment in time predicted by the prediction module 34A, or increase sampling of data from these devices. Note that all or a portion of the aforementioned hardware and/or software of the smartphone 14 may also be referred to herein as a processing circuit in some embodiments.

In some embodiments, all of the functionality of the proximity triggered sampling system may be implemented at the electronics device 14, and in some embodiments, functionality of the proximity triggered sampling system may be implemented among any combination of the electronics device 14, the wearable device 12, and the computing system 20. For instance, data collection may be achieved at the electronics device 14 (e.g., via image capture recording of heart rate, location tracking, beacon reception, etc.) and/or received at the electronics device 14 from wireless communications from the wearable device 12, and communicated to the computing system 20 for prediction processing. Messages and/or instructions for activation and/or increase/decrease of data collection functionality (e.g., data sampling) may be communicated from the computing system 20 to the electronics device 14 for implementation at the electronics device 14. In some embodiments, prediction processing and activation of messaging and/or data collection functionality may be performed entirely internal to the electronics device 14. In some embodiments, messages may be accessed from a remote data storage of the computing system 20 based on the prediction of an appropriate time to send messages. These and/or other variations may be implemented, and hence are contemplated to be within the scope of the disclosure.

Figure 4:
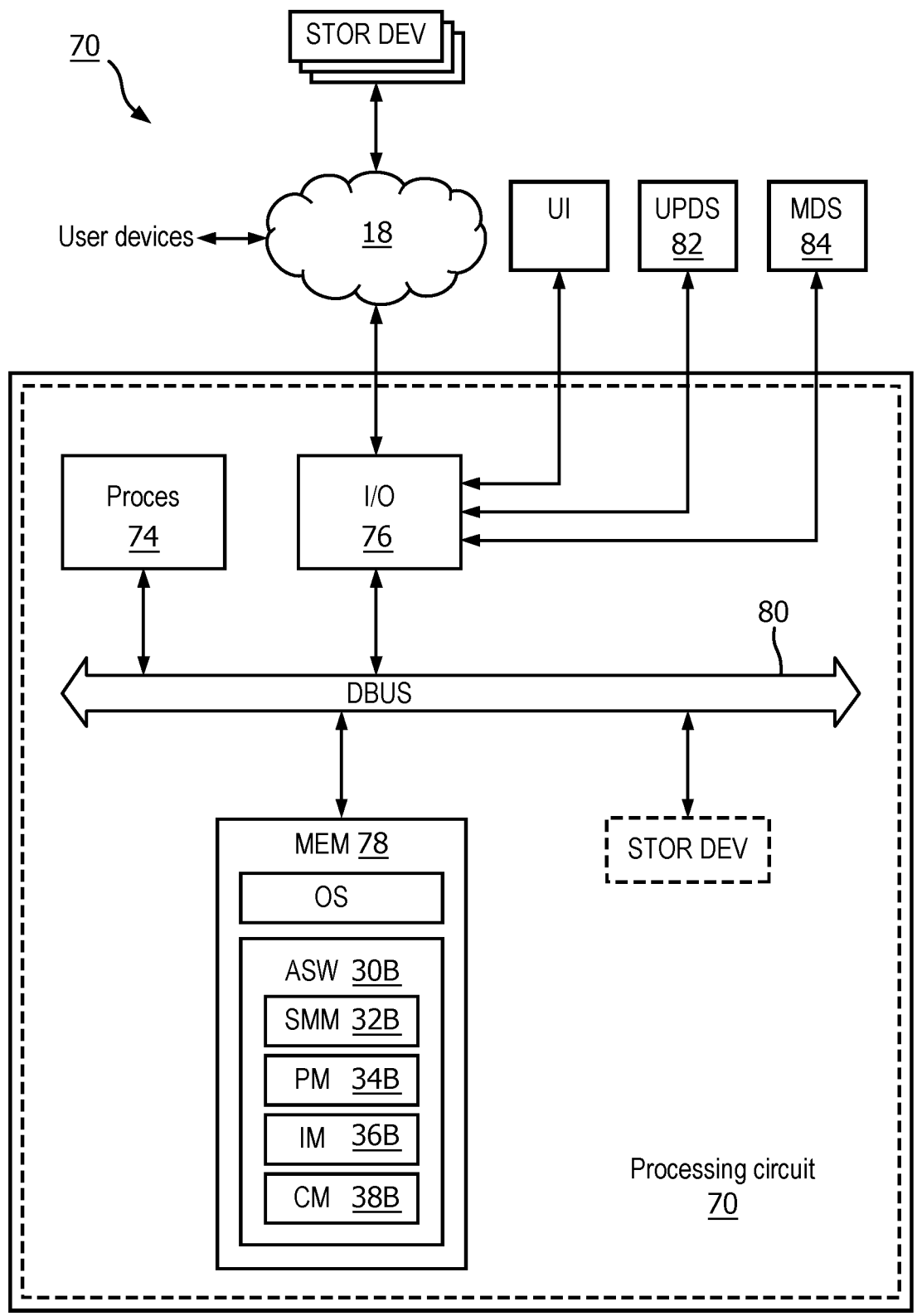
FIG. 4 is a schematic diagram that illustrates an example computing device in which all or a portion of the functionality of a proximity triggered sampling system may be implemented, in accordance with an embodiment of the invention.

Referring now to FIG. 4, shown is a computing device 70 that may comprise a device or devices of the remote computing system 20 (FIG. 1) and which may comprise all or a portion of the functionality of a proximity triggered sampling system. Functionality of the computing device 70 may be implemented within a single computing device as shown here, or in some embodiments, may be implemented among plural devices (i.e., that collectively perform the functionality described below). In one embodiment, the computing device 70 may be embodied as an application server device, a computer, among other computing devices. One having ordinary skill in the art should appreciate in the context of the present disclosure that the example computing device 70 is merely illustrative of one embodiment, and that some embodiments of computing devices may comprise fewer or additional components, and/or some of the functionality associated with the various components depicted in FIG. 4 may be combined, or further distributed among additional modules or computing devices in some embodiments. The computing device 70 is depicted in this example as a computer system, including a computer system providing functionality of an application server. It should be appreciated that certain well-known components of computer systems are omitted here to avoid obfuscating relevant features of the computing device 70. In one embodiment, the computing device 70 comprises a processing circuit 72 comprising hardware and software components. In some embodiments, the processing circuit 72 may comprise additional components or fewer components. For instance, memory may be separate from the processing circuit 72. The processing circuit 72 comprises one or more processors, such as processor 74 (PROCES), input/output (I/O) interface(s) 76 (I/O), and memory 78 (MEM), all coupled to one or more data busses, such as data bus 80 (DBUS). The memory 78 may include any one or a combination of volatile memory elements (e.g., random-access memory RAM, such as DRAM, and SRAM, etc.) and nonvolatile memory elements (e.g., ROM, Flash, solid state, EPROM, EEPROM, hard drive, tape, CDROM, etc.). The memory 78 may store a native operating system (OS), one or more native applications, emulation systems, or emulated applications for any of a variety of operating systems and/or emulated hardware platforms, emulated operating systems, etc. In some embodiments, the processing circuit 72 may include, or be coupled to, one or more separate storage devices.

For instance, in the depicted embodiment, the processing circuit 72 is coupled via the I/O interfaces 76 to user profile data structures (UPDS) 82 and a messages data structures (MDS) 84, explained further below. In some embodiments, the user profile data structures 82 and messages data structures 84 may be coupled to the processing circuit 72 directly via the data bus 80 (e.g., stored in a storage device (STOR DEV)) or coupled to the processing circuit 72 via the I/O interfaces 76 and the network 18 via one or more network-connected storage devices. In some embodiments, the user profile data structures 82 and messages data structures 84 may be stored in a single device or distributed among plural devices. Though depicted in association with the computing device 70, some embodiments of a proximity triggered sampling system may use the data structures 82 and/or 84 locally to the user devices (e.g., at the wearable device 12 and/or the electronics device 14). Though described as separate data structures, in some embodiments, the content stored by the user profile data structures 82 and messages data structures 84 may be combined into a single data structure. The user profile data structures 82 and messages data structures 84 may be stored in persistent memory (e.g., optical, magnetic, and/or semiconductor memory and associated drives). In some embodiments, the user profile data structures 82 and messages data structures 84 may be stored in memory 78.

The user profile data structures 82 are configured to store user profile data. In one embodiment, the user profile data comprises demographics and user data, including physiological data and contextual data corresponding to user monitored activity. Contextual data may be communicated from the wearable device 12 and/or the electronics device 14, or from other devices. For instance, some user contextual data may be collected from existing personal resources, including from social media websites or from a blog or from a patient sharing group, calendars of the user or of people with whom the user interacts, among other sources. The user profile data structures 82 may be accessed by the processor 74 executing software in memory 78 to supplement proximity data received from the wearable device 12, electronics device 14, and/or other devices, enabling a prediction of user state changes and ultimately a moment in time to change messaging function characteristics and/or data collection function characteristics at the computing system 20 (or communicating the message or instructing the same functionality at the wearable device 12 and/or electronics device 14).

The messages data structure 84 comprises predefined messages (e.g., one way messages, two-way messages) to be communicated to the user devices 12 and/or 14, and in some embodiments, may include a template or be updated manually or via a machine learning algorithm (e.g., regression, random forest, (deep) neural networks, etc.) to personalize the messages. In some embodiments, one or more of the content stored in the user profile data structures 82 may also be stored as meta information in the messages data structures 84.

The user profile data structure 82 may also include current or contemporaneous activity data for the user that is communicated to the computing device 70 during synch operations with the smartphone 14 and/or wearable device 12 or as communicated from a third party server device (e.g., medical facility, fitness tracking service, etc.). Additional data structures may be used to record similar information for other users. The user profile data structures 82 may be updated periodically, aperiodically, and/or in response to one or more events.

In the embodiment depicted in FIG. 4, the memory 78 comprises an operating system (OS) and application software (ASW) 30B, the latter which may execute a health and wellness program, among other programs in some embodiments. The application software 30B comprises a plurality of software modules (e.g., executable code/instructions) including the sensor measurement module (SMM) 32B, a prediction module (PM) 34B, an interface module (IM) 36B, and a communications module (CM) 38B. In some embodiments, the application software 30A may include additional or fewer software modules and/or functionality. The sensor measurement module 32B analyzes measurements and/or user-inputted profile data from the wearable device 12 and/or smartphone 14 (e.g., accessed from the user profile data structure 82) as part of the health and wellness program. For instance, the sensor measurement module 32B receives and analyzes the activity data, environmental data, physiological data, psychological data, location data, demographics, etc. of or corresponding to the user and provides a dashboard of information that may include progress towards a given goal (e.g., fitness goals), comparisons to the general population (or user-configured population of people), and/or performance data for various activities (e.g., physiological measurements, derived measurements including caloric loss, energy expenditure, etc.). The sensor measurement module 32B may also provide feedback to the prediction module 34 as to the physiological state of the user based on the physiological measures. The communications module 38B receives the activity data/user profile data and proximity data and other contextual data from the wearable device 12 and/or electronics device 14, and also communicates electronic messages and/or instructions to the wearable device 12 and/or the electronics device 14. The communications module 38B generally enables communications among network-connected devices and provides web and/or cloud services, among other software such as via one or more APIs. In some embodiments, the communications module 38B may be separate from the application software 30B. In one example operation, the communications module 38B may receive (via I/O interfaces 76) input data from the wearable device 12 and/or the electronics device 14 that includes sensed data (e.g., proximity data, physiological data, environmental data, location data, etc.), context data, user-inputted data, data from third-party databases (e.g., medical data base, health program provider data, etc.), data from social media (e.g. from other computing devices), data from external devices (e.g., weight scales, optionally environmental sensors, etc.), among other data. The input may be continual, intermittent, and/or scheduled. The communications module 38B may, in one embodiment, be activated by the application software 30B based on a determined meaningful moment (by the prediction module 34B) to communicate electronic messages to the wearable device 12 and/or electronics device 14 that are informational and do not require or solicit a user reply (e.g., one-way messages) or that solicit user input (e.g., two-way messages). In some embodiments, the communications module 38B may cooperate with the interface module 36B to provide web services for the wearable device 12 and/or electronics device 14, enabling the access and download of web pages to enable the user, using browser functionality in the wearable device 12 and/or electronics device 14, to receive messages and optionally reply to messages. In general, the communications module 38B may comprise a web service component or cloud component which is accessed by a client application (e.g., browser, etc.) residing at the wearable device 12 and/or electronics device 14.

Execution of the application software 30B (including software modules 32B-38B) may be implemented by the processor 74 under the management and/or control of the operating system. The processor 74 may be embodied as a custom-made or commercially available processor, a central processing unit (CPU) or an auxiliary processor among several processors, a semiconductor based microprocessor (in the form of a microchip), a macroprocessor, one or more application specific integrated circuits (ASICs), a plurality of suitably configured digital logic gates, and/or other well-known electrical configurations comprising discrete elements both individually and in various combinations to coordinate the overall operation of the computing device 70.

The I/O interfaces 76 comprise hardware and/or software to provide one or more interfaces to the Internet 18, as well as to other devices such as a user interface (UI) (e.g., keyboard, mouse, microphone, display screen, etc.) and/or the data structures 82-84. The user interfaces may include a keyboard, mouse, microphone, immersive head set, display screen, etc., which enable input and/or output by an administrator or other user. The I/O interfaces 76 may comprise any number of interfaces for the input and output of signals (e.g., analog or digital data) for conveyance of information (e.g., data) over various networks and according to various protocols and/or standards. The user interface (UI) is configured to provide an interface between an administrator or content author (e.g., for the generation of messages or message templates) and the computing device 70. In one embodiment, the user interface enables the administrator to craft the message templates, and once defined, the messages may be generated automatically (and updated via learning algorithms). The administrator may input a request via the user interface, for instance, to manage the user profile data structures 82 and/or the messages data structures 84. Updates to the data structures 82 and/or 84 may also be achieved without administrator intervention.

When certain embodiments of the computing device 70 are implemented at least in part with software (including firmware), as depicted in FIG. 4, it should be noted that the software (e.g., including the application software 30B (and associated modules 32B-38B) can be stored on a variety of non-transitory computer-readable medium for use by, or in connection with, a variety of computer-related systems or methods. In the context of this document, a computer-readable medium may comprise an electronic, magnetic, optical, or other physical device or apparatus that may contain or store a computer program (e.g., executable code or instructions) for use by or in connection with a computer-related system or method. The software may be embedded in a variety of computer-readable mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the computing device 70 are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), relays, contactors, etc.

Figure 5:
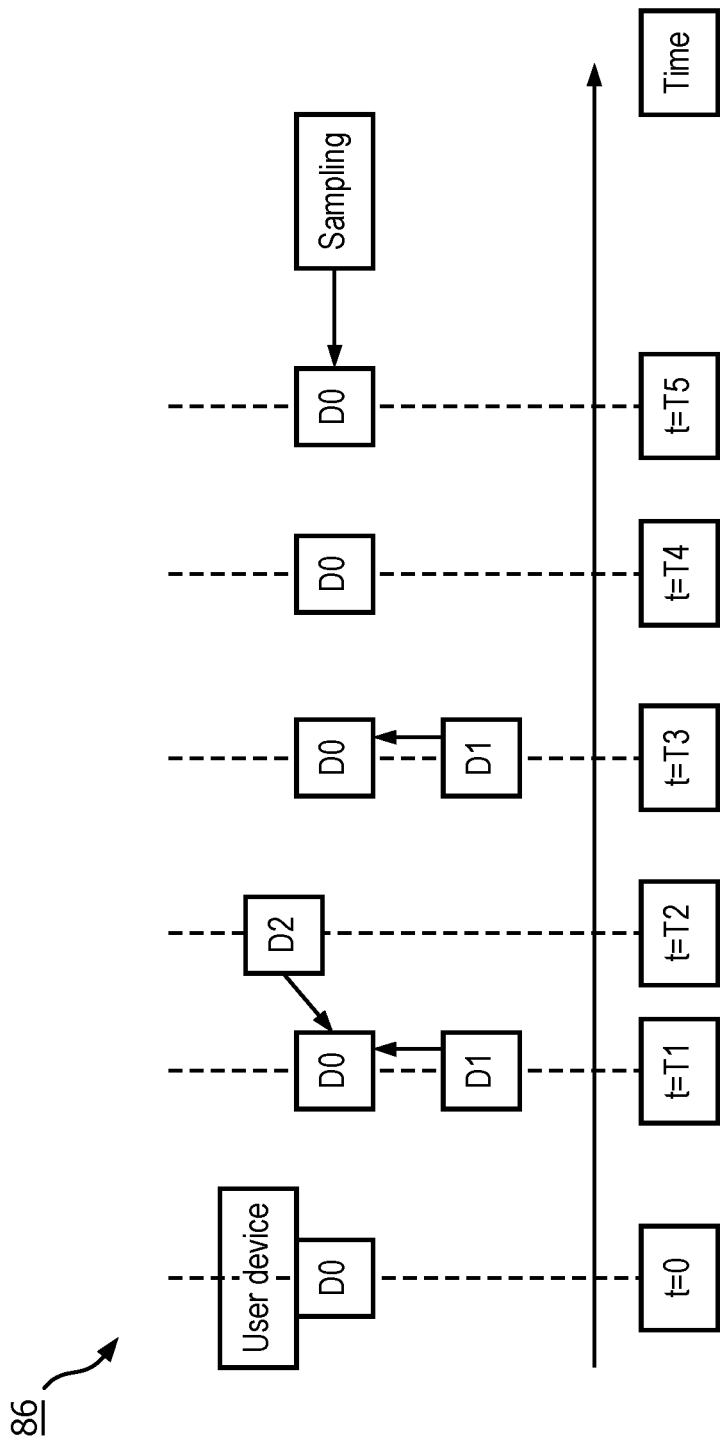
FIG. 5 is a schematic diagram that illustrates example changes in proximity information as a function of time, in accordance with an embodiment of the invention.

Referring now to FIG. 5, shown is a schematic diagram 86 that illustrates example changes in proximity information as a function of time according to an embodiment of a proximity triggered sampling system. The diagram 86 shows a timeline (on the horizontal axis, t=0 through t=T5) of social interactions between users as detected via beacon communications (or other proximity detection technology, including Wi-Fi) among user device D0 and other user devices D1 and D2. The timeline of social interactions help illustrate an example where a meaningful sampling moment corresponding to a change in state of the user (of D0) is predicted (e.g., by the prediction module 34, 34A, or 34B of FIGS. 2-4). Digressing briefly, the proximity triggered sampling system operates under several premises, namely that interactions with other people influence a user's emotional state, and the emotional state changes originating from person-to-person interactions depend on the number of people involved in the interaction, the duration of interaction, and potentially other features, such as location of interaction, and people involved. Since it is highly likely that user state (e.g., emotional) will change as a result of an interaction, it is more likely to get a representative description of the user state, by sampling at these moments, instead of at random times. The premise of user state changes as a result of interacting with others has been supported by experimental data of the assignee of the present application, and other research. For instance, experimental data has shown that users' heart rate and emotions changes as a result of social interactions with others. The findings also suggest that the number of people involved in the interaction can also play a role in how user state changes. Interaction characteristics can be unobtrusively monitored using proximity sensors (e.g., beacon technology, such as iBeacon®) in the user devices D0-D3. Certain embodiments of a proximity triggered sampling system monitors the proximity characteristics, to detect the change points in time, and to push to a user a timely message (e.g., one-way, two-way) and/or implement a change in data collection function characteristics at these moments. In FIG. 5, the application software 30 of the D0 detects when person-to-person interactions have commenced and ended (e.g., the number of devices in the proximity of user changes from greater than 1 to 0) and uses these moments to cause a change in messaging function characteristics (e.g., push an emotional state question) and/or data collection function characteristics. More specifically, in FIG. 5, it is observed that at time t=0, the observed user (user 0, using D0) is alone. At t=T1 the user is having a social contact with one person, and at time T2, with two people (e.g., corresponding to devices D2 and D1). At T3 the interaction is only with one person again. The interaction ends at T4, and the intervention (sampling) is delivered (or initiated/activated) at T5.

Figure 6:
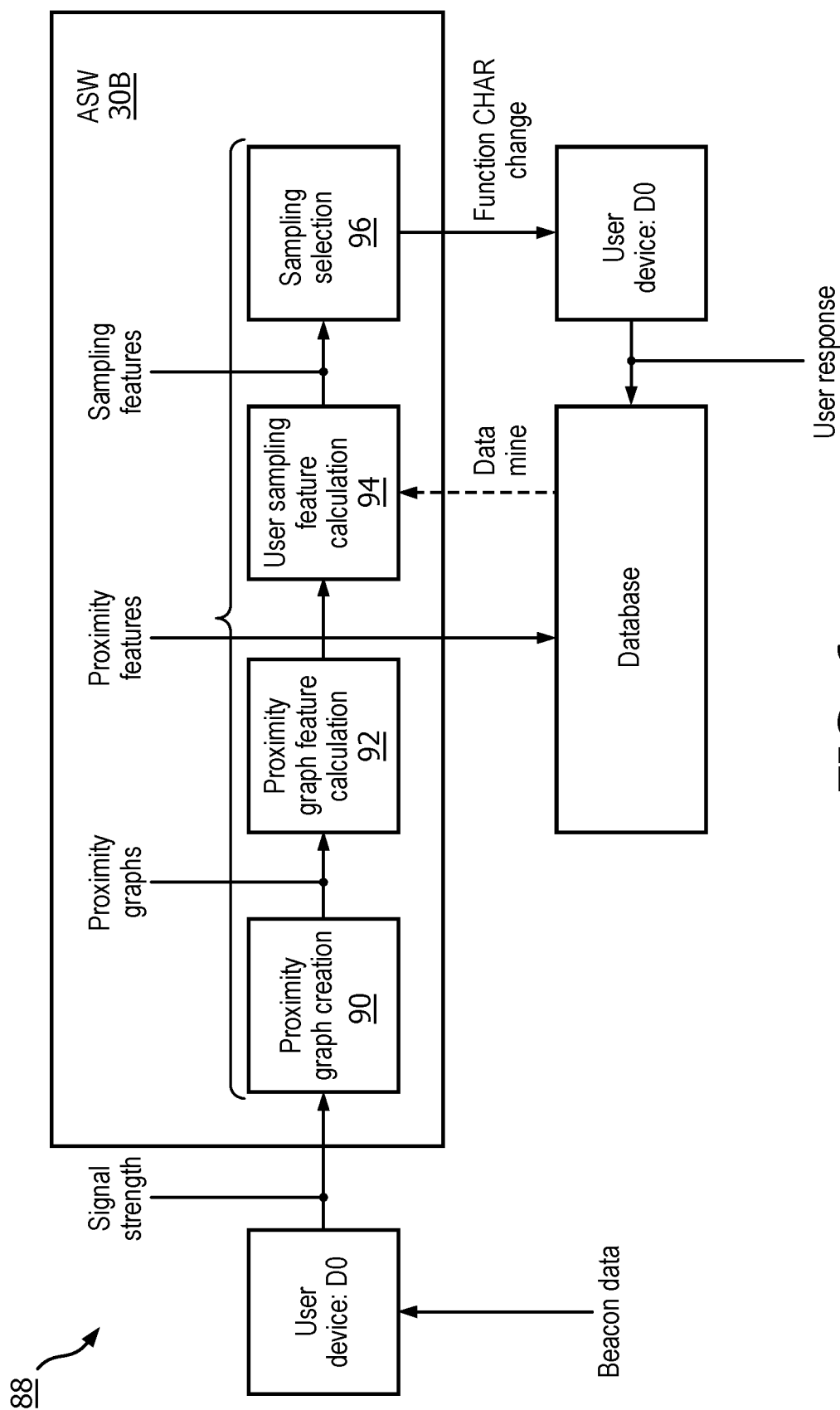
FIG. 6 is a flow diagram that illustrates an example proximity triggered sampling process, in accordance with an embodiment of the invention.

Referring now to FIG. 6, shown is a flow diagram that illustrates an example proximity triggered sampling process 88. It should be appreciated by one having ordinary skill in the art, in the context of the present disclosure, that the process 88 depicted in FIG. 6 is but one example, and that in some embodiments, the process 88 may have additional or fewer steps. The process 88 assumes prediction processing (e.g., by the application software 30B executing in the computing system 20, and in particular, the computing device 70 (FIG. 4), such as via a cloud platform implementation), with the computing device 70 receiving data from, and communicating messages and/or instructions to, user device D0 (e.g., a wearable device 12 or electronics device 14, FIG. 1). It should be appreciated by one having ordinary skill in the art that the depicted example is illustrative of one embodiment, and as indicated above, the prediction processing may be performed at one or more of the user devices in some embodiments. As illustrated in FIG. 6, the user device (D0) detects other user devices, each of the user devices equipped with proximity sensing functionality (e.g., iBeacon devices, Wi-Fi, etc.). Using beacon signal strength information, the application software 30B creates proximity graphs (90). Changes in the proximity graphs are monitored in real time by the application software 30B, and proximity features are calculated (92) by the application software 30B (e.g., prediction module 34B). Based on the proximity features (and in some embodiments, user data), sampling method characteristics (e.g., content-related and/or non-content related message features, including EMA (e.g., message) type, content, time, such as determining when to ask the user a question based on changes in the proximity graph may be based on changes in ego density, etc.) are determined (94), which are then used to select the appropriate sampling content (96), which is then delivered as a change in message function characteristics and/or data collection function characteristics (e.g., deliver a message, instructions to start a measurement, etc.) to the user's device D0. Note that in some embodiments, selection (96) may be replaced with, or supplemented by, generation. For instance, templates (or rules or natural language processing algorithms) may be used and the content to be communicated to the user may be automatically generated as described previously.

The user response is tracked and stored in a database (e.g., user profile data structure 82, FIG. 4), together with the proximity features. Using the (historical) information in the database, sampling feature calculation and selection can be improved (for example personalized according to the user, devices in the proximity graph, location, etc.) by applying data mining techniques. For instance, learning algorithms may be used to determine the best way to communicate with the user. If, for certain combinations of the proximity features and sampling content features, it is observed that the user is not responsive, then this information can be taken into account in future calculations. For example, if the proximity triggered sampling system learns that after a 1-1 meeting that happens regularly on Friday, the user is always responding, this can result in increasing the number of questions that are asked after this meeting. In some embodiments, the proximity triggered sampling system uses multiple data sources/features, which include proximity features, sampling content features (also including time, environment, lexicon, semantics, sentiments, etc.), user state features, for example if the user is tracking HR, movements, speech, temperature, etc., and user input features (e.g., how the user has responded in the past). The aforementioned sources/features are processed together to find/predict what is the best combination of these sources/features. In one embodiment, based on the three or more of the stored user response, the user state, features correspond to sampling, or the proximity features, the system enhances future proximity feature computations and the features corresponding to the sampling.

Note that the description of the process 88 above describes the determination of the sampling method characteristics based on proximity data, and in some embodiments, proximity data and user data (user features). Certain embodiments of a proximity triggered sampling system predict potential points in time to sample for the user's subjective input. To determine these sampling moments and sampling characteristics, in one embodiment, all available data may be used, including (objective) proximity real-time characteristics, (objective) real time user data characteristics (e.g., heart rate, etc.), past (subjective) user input data characteristics, and past (objective) proximity and user data characteristics.

Figure 7:
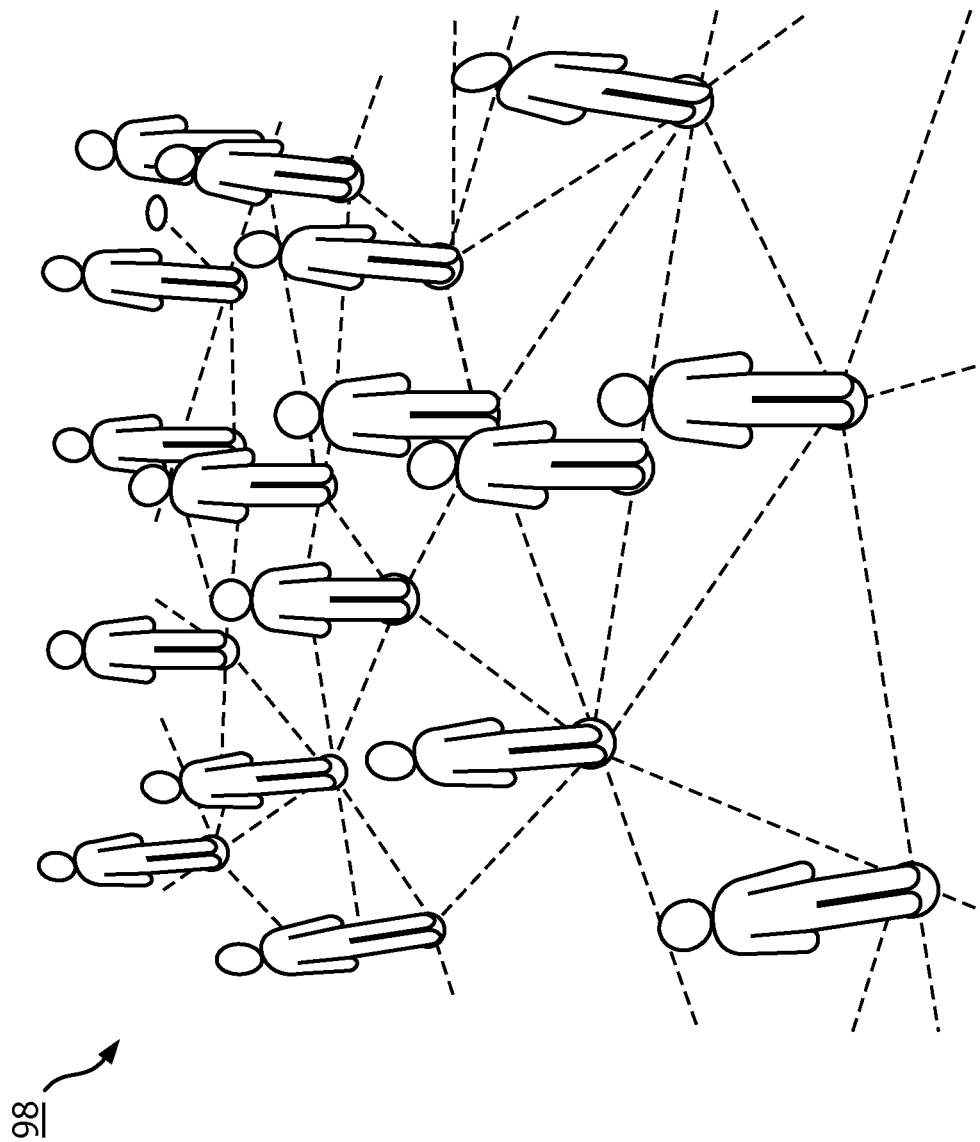
FIG. 7 is a schematic diagram that illustrates an example proximity graph, in accordance with an embodiment of the invention.

With continued reference to FIGS. 5-6, attention is directed to FIG. 7, which schematically illustrates an example proximity graph 98. Certain embodiments of a proximity triggered sampling system (e.g., the prediction module 34B of the application software 30B) make use of the proximity graphs 98 to monitor the proximity of users in real time. The proximity graph 98 correspond to a proximity of one or more other devices to a user device and to each other. Changes in the proximity information determined from the proximity graphs 98 are detected in real time, and this information (among other information in some embodiments) is used as a trigger to change (e.g., activate, increase, decrease) messaging function characteristics and/or a data collection function characteristics (e.g., to deliver the EMAs, or in general, messages and/or sample or collect user data). The proximity graphs 98 comprise a computational structure that represents the proximity of devices (e.g., wearable devices 12 and/or electronic devices 14). Nodes in the proximity graph 98 are devices, and an edge indicates that these devices are in proximity.

In one embodiment, the prediction module 34B monitors the changes in the proximity graph in real time based on the calculation by the prediction module 34B of proximity features, which includes any one or combination of a density of the proximity graph 98, a number of connections (e.g., where connections refer to a condition where a user device is receiving a strength signal (above a certain threshold) and for a specific time (above a certain threshold) that can be interpreted that the user is in proximity/interaction with the owner of that device) of an individual, a rate of change of connections, a duration of particular connections, and an identity (e.g., device IDs) of connections, and proximity features corresponding to devices of other users in proximity to the user (e.g., a user may be in contact with user A, and if accessible, the proximity features from user A's device may also be considered a proximity feature for the current user). In one embodiment, an interaction (e.g., social interaction) is defined as (at least) one other device (D1) being in proximity of a user's device (D0) for more than two (2) minutes, and then (after a specific, predetermined time, say in seconds (e.g., less than 60 seconds)) no device being in the proximity of D0, after D1 (or more devices if that is the case) leaves. A start of the social interaction is the moment D0 and D1 get in sufficient proximity of each other, and an end of the social interaction is when D1 is no longer in sufficient proximity of D0. What is deemed a sufficient proximity may be dependent on the number of devices in proximity of D0. For instance, referring to the interpersonal distances of man (defined by Edward T. Hall's work in the field of Proxemics), in the case of a single device, the distance is defined as being less than 1.2 meters; in the case of two or three devices, the distance is defined as being less than 2.1 meters; and in the case of more than three devices, the distance is defined as being less than 3.7 meters. Note that other definitions for determining the sufficiency of proximity to other devices may be used, depending on the conditions and/or goals or other design constraints of the system and/or environment in which the system is used. The distance between devices is approximated from the iBeacon signal strength in which a greater signal strength indicates a shorter distance. An example method to calculate distances using iBeacon® (a protocol developed by Apple®) may be found in technical forums, such as on-line stack overflow forums on iBeacon® distancing, which provides that the distance estimate provided by iOS is based on the ratio of the iBeacon (e.g., formatted as several bytes including a unique identifier recognized by compatible devices/applications) with signal strength (RSSI) over the calibrated transmitter power (txPower). The txPower is the known measured signal strength in RSSI at one (1) meter away. Each iBeacon must be calibrated with this txPower value to allow accurate distance estimates.

The prediction module 34B triggers assessments (e.g., sampling) based on the calculated proximity features. In one example, the density of a subgraph within the proximity graph increases quickly, which may imply that nodes within that subgraph have formed an (adhoc) meeting. If after a certain period of time, for instance twenty (20) minutes, the density of the subgraph quickly decreases, this means that the meeting has ended. These two observations, the forming of a group and the subsequent dissolving of that group, provide a suitable pattern for sending a message to members of the group. Using signal strength information from the iBeacons, kinesthetic factors related to the distance between participants can be calculated. The user state change is related to the change in proximity graphs, which is a result of an observed change in the monitored signal strengths. In other words, greater user emotional state changes can be expected as a result of closer proximity interactions. In one embodiment, the prediction module 34B detects the start and end of social interaction, as described above, and delivers a message (or in general, samples user (sensor) data) shortly (e.g., within sixty (60) seconds) after the end of the interaction.

In some embodiments, social interaction features can be approximated from the proximity graph features, and these can be used while determining the moment and type (content) of messages. A non-exhaustive list of examples of interaction features that can be extracted from the proximity graphs and how they can be used for triggering and selecting messages are shown in the following Table 1.

TABLE 1

| Proximity graph feature | EMA feature | Explanations | Logic |
|---|---|---|---|
| Meeting duration | Delivery time | Delivery time of EMA is determined as a function of a meeting duration. E.g. If the meeting was short (<=30 min) deliver the questionnaire 1 min after end of the meeting. If the meeting was long (>30 min), deliver the questionnaire 5 min after end of the meeting. | People need more recovery time after long meetings |
| Meeting duration | Number of questions | Questionnaire length is a function of meeting | More user state factors change |

TABLE 1-continued

| Proximity graph feature | EMA feature | Explanations | Logic |
|---|---|---|---|
| | | duration. After short meetings use shorter questionnaires (e.g. 2 questions), and after long meeting use longer questionnaires (e.g. 4 questions). | after longer meetings |
| Number of people in the meeting | (Emotion) question specificity and detail | The amount of details asked from the user is a function of number of people that were present in the meeting. After meetings with less than 4 people ask more specific or detailed questions. For example, in addition to asking the users to select or input their emotions also ask them to rate the strength of their emotion. | Emotions are more influenced in small group meetings |
| Proximity of people in the meeting | Context and location questions | Ask questions related to the context and location if proximity of participants is different than normal | Context determines how close people will stay during meetings |
| Identity of people in the meeting, or type (e.g. colleagues) or role (e.g. direct manager) of the people in the meeting | Person specific questions | Ask questions specific to the people present in the meeting | Who is present in the meeting can strongly influence how emotions change |

Table 1 illustrates an example look-up table that illustrates how messages may be selected based on assessments of the proximity graph features. Note that the various features presented in Table 1 are only some specific example, which do not cover all possible combinations. In general, certain embodiments of a proximity triggered sampling system can model the question parameters as a function of all or a portion of the proximity features. One relationship between proximity features and the message features can be represented using a rule-based look up table approach as shown in Table 1, or can be modelled by the prediction module 34B as a mathematical function, or in some embodiments, a data mining approach (e.g. using neural networks) can be used.

Although the various embodiments have been described in the context of human-human social interactions, in some embodiments of a proximity triggered sampling system, human-computer interaction changes may be monitored in an effort to predict potential sampling methods. For example, user engagement in a conversation with a virtual agent/assistant (e.g., chatbot) can be detected, and the message can be delivered (or in general, a message function characteristic changed) when the interaction is over (and/or a data collection function characteristic may be changed). Such detection may be via detection of a switch or button selection on the device and/or from detection of movement (e.g., gestures) if the device is equipped with movement sensors, such as accelerometers. A signal received from the machine/computer/device that the user is communicating with may be used in some embodiments to indicate a status of the communications or interactions (e.g., start, end, continuing, etc.).

Further, though operations have been emphasized using proximity data as input to the prediction module 34B, in some embodiments, other sensor data may be used, wherein a context of the social interaction can be detected and the sampling can be adapted accordingly. For example, if GNSS data (e.g., GPS data) is available, social interactions can be differentiated as between-family or between work colleagues. Another example is using accelerometer data, where a user activity may be detected, including running or exercising in the gym together with social partners. Other examples include, without limitation, monitoring of speech (e.g., voice) and/or dialog characteristics, monitoring of facial and/or facial features (e.g., lips, eyes, etc.), monitoring of gestures (e.g., head, hands, torso, legs, etc.). Depending on the context information, the type and content of the messages can be adapted. In an example implementation, different messaging options and their relation to the user context can be stored in a look-up table. Further, though proximity data is described as a mechanism for detecting a user interaction for the prediction of user state change, other and/or additional mechanisms may be used for detection of interactions (with machine or humans), include voice detection using microphones, meetings via an electronic calendar, SKYPE conversations, social media/website conversations, etc.

In view of the description above, it should be appreciated that one embodiment of a computer-implemented, proximity triggered sampling method, depicted in FIG. 8 and referred to as a method 100 and encompassed between start and end designations, comprises receiving data corresponding to an interaction with a user (102); based on the received data, predicting a moment in time when a state of the user is likely to change (104); and causing a change in one or a combination of message function characteristics or data collection function characteristics at the moment in time (106). The change may involve activation of message function characteristics or data collection function characteristics, or an increase or decrease in either or both the message function characteristics or data collection function characteristics. Message function characteristics include whether the message function is activated or not, a frequency of the messaging, a content or type of the message, one or any combination of length, size, duration of the message, a delivery time of the message, among other characteristics. Data collection function characteristics include whether the data collection is activated or not, a start and stop time of the data collection, a frequency of the data collection, the type of measurement function, a delivery time of the data collection function, among other characteristics. For instance, an activation of the message function characteristics may involve communicating messages (one-way or two-way messages) at a meaningful moment in time. An example of an increase of, say, a data collection function characteristic may involve increased sampling of a heart rate measurement, or tracking (GNSS) function. Also, an example of a decrease of say, a message function characteristic may be realized in scenario that, since the sampling characteristics other than time can also change, a user may be confronted with a decreased number of questions depending on the observed proximity and user features. Also, the state of the user may include one or any combination of the psychological or physiological state of the user. For instance, the psychological state may include the affective or emotional state, states of readiness, curiosity, absorbed, or conscious, to name a few. The physiological state may manifest itself where a user has just left a long meeting and is tired, and/or the physiological state may be reflected by readings of the sensors (e.g., heart rate, blood pressure, skin temperature, VO2max, etc.).

Any process descriptions or blocks in flow diagrams should be understood as representing modules, segments, or portions of code which include one or more executable instructions for implementing specific logical functions or steps in the process, and alternate implementations are included within the scope of the embodiments in which functions may be executed out of order from that shown or discussed, including substantially concurrently or in reverse order, depending on the functionality involved, as would be understood by those reasonably skilled in the art of the present disclosure.

Though various embodiments of a proximity triggered sampling system have been disclosed in the context of a lifestyle application, it should be appreciated by one having ordinary skill in the art that applications for the proximity triggered sampling system may be extended to other fields, including healthcare environments (e.g., as an application for patients and healthcare providers), commercial applications (e.gh., monitoring the state of shoppers to provide relevant coupons), education environments (e.g., providing monitoring and interaction options for students or teachers), and business (e.g., as a tool for monitoring productiveness and/or user satisfaction). As another example, certain embodiments of a proximity triggered sampling system may be used in the financial industry, wherein the proximity triggered sampling system may enable a user to make an investment when in a proper state of mind. Further, messages may vary depending on various demographics, including gender. For instance, messages may be delivered that are more suitable to a man than a woman.

As a further example of variations to the above-description of certain embodiments of a proximity triggered sampling system, though textual feedback (presentation of the messaging) has been described as via the wearable device 12 and/or electronics device 14, feedback messaging may be presented audibly (in lieu of, or in addition to text) via speaker functionality of either device 12, 14 (FIG. 1) and/or visibly (e.g., video playback of an avatar). In some embodiments, the messaging may be conveyed via a third party. For instance, the messages may be delivered to a third person (e.g., the user's coach or trainer or mentor) and in turn conveyed verbatim or substantially verbatim by the third person. The message may be delivered, for instance, to an earpiece worn by the third person and relayed by the third person to the user.

Note that various combinations of the disclosed embodiments may be used, and hence reference to an embodiment or one embodiment is not meant to exclude features from that embodiment from use with features from other embodiments. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical medium or solid-state medium supplied together with or as part of other hardware, but may also be distributed in other forms. Any reference signs in the claims should be not construed as limiting the scope.

The invention claimed is:

1. A system, comprising:
memory comprising instructions; and
one or more processors configured to execute the instructions to:
monitor respective strengths of beacon signals of one or more other devices to a user device of a user, wherein monitoring the respective strengths of the beacon signals comprises determining proximity features indicative of social interactions of the user;
based on the proximity features indicating a social interaction, predict a moment in time when a state of the user is likely to change, wherein the state of the user comprises a psychological state of the user; and
cause, at the moment in time, one or more assessments based on the proximity features, wherein causing the one or more assessments comprises:
changing message function characteristics at the moment in time;
changing data collection function characteristics at the moment in time; and
communicating a message to the user at the moment in time.

2. The system of claim 1, wherein the one or more processors are further configured to execute the instructions to change the message function characteristics by activating, and/or increasing, the message function characteristics at the moment in time.

3. The system of claim 1, wherein changing the message function characteristics comprises communicating a message to the user at the moment in time, and wherein the message comprises a two-way communication message that solicits direct feedback from the user, wherein the message is communicated locally or remotely.

4. The system of claim 1, wherein the one or more processors are further configured to execute the instructions to change the data collection function characteristics by increasing the data collection function characteristics.

5. The system of claim 1, wherein the system further comprises one or more sensors configured to generate other sensor data, wherein the one or more processors are further configured to execute the instructions to further predict the moment at least by determining how the other sensor data is changing in time and determining if the other sensor data differs from a set of data already collected.

6. The system of claim 1, wherein the one or more processors are further configured to execute the instructions to determine one or more characteristics associated with social interactions of the user based on the strengths of beacon signals.

7. The system of claim 6, wherein the one or more processors are further configured to execute the instructions to predict the moment further based on the monitoring to detect when a number of devices in sufficient proximity to a user device has changed.

8. The system of claim 1, wherein the beacon signals are received in real time, and wherein the one or more processors are further configured to execute the instructions to:
repeatedly generate proximity graphs based on the strength of the beacon signals, the proximity graphs corresponding to the proximity of the one or more other devices to the user device and to each other;
compute the proximity features based on changes in the proximity graphs monitored in real time;
store the proximity features in a data storage device;
determine sampling method characteristics based on the proximity features; and
select or generate a message based on the determination.

9. The system of claim 8, wherein the one or more processors are further configured to execute the instructions to:
track a user response to the message;
store the user response in the data storage device; and
based on three or more of a stored user response, the user state, features correspond to sampling, or the proximity features, enhance future proximity features and/or their computations and the features corresponding to the sampling and/or their computation.

10. The system of claim 8, wherein the proximity features comprise any one or a combination of a proximity between the user device and the one or more other user devices, a density of each proximity graph, a number of connections between the user device and the one or more other devices, a duration of each of the connections, an identity of each of the connected devices, or proximity features corresponding to one or more devices in proximity of the user device, wherein each connection corresponds to the user device receiving a strength signal above a threshold for a time above a threshold amount of time.

11. The system of claim 10, wherein the one or more processors are further configured to execute the instructions to associate an interaction between a user and another user based on a connection of the user device to another device, wherein a start of the interaction is based on a sufficient proximity of the user device to the another user device for a specific length of time and an end of the interaction is based on a subsequent termination of sufficient proximity between the user device and the another user device.

12. The system of claim 11, wherein the one or more processors are further configured to execute the instructions to change the message function characteristics by activating the message function characteristics a specific time after an end of the interaction, which corresponds to the moment in time.

13. The system of claim 1, wherein the one or more processors are part of a cloud computing platform or a user device.

14. The system of claim 1, wherein the one or more processors are further configured to execute the instructions to predict the moment in time when the state of the user is likely to change further based on sensed human-device interactions and signals from one or more additional sensors.

15. The system of claim 14, wherein the signals from one or more additional sensors comprises user device position data, environmental data, facial characteristic data, voice data, and user movement data.

16. The system of claim 14, wherein the one or more processors are further configured to execute the instructions to cause activation or adaptation of the communication function characteristics and the data collection function characteristics when the human-device interaction has ended.

17. The system of claim 1, wherein the one or more processors are configured to execute the instructions to predict the moment in time when the state of the user is likely to change using a trained machine learning model, the machine learning model trained based on prior data corresponding to prior interactions with the user, prior predicted moments in time, prior messages communicated to the user, and user responses to the prior messages.

18. The system of claim 1, wherein the one or more processors are configured to execute the instructions to determine content of the message to the user using a trained machine learning model, the machine learning model trained based on prior data corresponding to prior interactions with the user, prior predicted moments in time, prior messages communicated to the user, and user responses to the prior messages.

19. The system of claim 1, wherein the respective signal strengths indicate proximities of one or more other devices to the user device, and to each other.

20. The system of claim 1, wherein predicting the moment in time comprises determining distances between the user device and the one or more other devices based on the respective strengths, the distances being indicative of the social interaction, and, based on the determined distances, predict the moment in time.

21. The system of claim 1, wherein data collection function characteristics comprise a start or stop of a heart rate measurement, a sampling frequency, and/or a memory capacity.

22. The system of claim 1, wherein determining the proximity features comprises determining a proximity graph that corresponds to a proximity of the one or more other devices to the user device and to each other, and determining a density of a sub graph within the proximity graph that increases when the one or more other devices are in close proximity to the user device and/or to each other; and
wherein the moment in time when the state of the user is likely to change is predicted based on the density of the sub graph.

23. A non-transitory computer readable medium comprising executable code that, when the code is executed by one or more processors, causes the one or more processors to:
monitor respective strengths of beacon signals of one or more other devices to a user device of a user, wherein monitoring the respective strengths of the beacon signals comprises determining proximity features indicative of social interactions of the user;
based on the proximity features indicating a social interaction, predict a moment in time when a state of the user is likely to change, wherein the state of the user comprises a psychological state of the user; and cause, at the moment in time, one or more assessments based on the proximity features, wherein causing the one or more assessments comprises:
  changing message function characteristics at the moment in time;
  changing data collection function characteristics at the moment in time; and
  communicating a message to the user at the moment in time.

24. A computer-implemented method, comprising:
monitoring respective strengths of beacon signals of one or more other devices to a user device of a user, wherein monitoring the respective strengths of the beacon signals comprises determining proximity features indicative of social interactions of the user;
based on the proximity features indicating a social interaction, predicting a moment in time when a state of the user is likely to change, wherein the state of the user comprises a psychological state of the user; and
causing, at the moment in time, one or more assessments based on the proximity features, wherein causing the one or more assessments comprises:
  changing message function characteristics at the moment in time;
  changing data collection function characteristics at the moment in time; and
  communicating a message to the user at the moment in time.

* * * * *